(12) United States Patent
Sharabani

(10) Patent No.: US 11,806,248 B2
(45) Date of Patent: *Nov. 7, 2023

(54) EXPANDABLE IMPLANT

(71) Applicant: SeaSpine, Inc., Carlsbad, CA (US)

(72) Inventor: Netanel Sharabani, Rishpon (IL)

(73) Assignee: SeaSpine, Inc., Carlsbad, CA (US)

( * ) Notice: Subject to any disclaimer, the term of this patent is extended or adjusted under 35 U.S.C. 154(b) by 373 days.

This patent is subject to a terminal disclaimer.

(21) Appl. No.: 17/035,301

(22) Filed: Sep. 28, 2020

(65) Prior Publication Data

US 2021/0077271 A1  Mar. 18, 2021

Related U.S. Application Data

(63) Continuation of application No. 16/322,019, filed as application No. PCT/IL2017/050828 on Jul. 23, 2017, now Pat. No. 10,786,367.

(Continued)

(51) Int. Cl.
  *A61F 2/44* (2006.01)
  *A61F 2/46* (2006.01)
  *A61F 2/30* (2006.01)

(52) U.S. Cl.
  CPC ............ *A61F 2/447* (2013.01); *A61F 2/4455* (2013.01); *A61F 2/4611* (2013.01);
  (Continued)

(58) Field of Classification Search
  CPC .. A61F 2002/30535–3054; A61F 2/447; A61F 2/4455
  See application file for complete search history.

(56) References Cited

U.S. PATENT DOCUMENTS 5,554,191 A  9/1996 Lahille
6,159,244 A  12/2000 Suddaby
(Continued)

FOREIGN PATENT DOCUMENTS

EP  3487448  5/2019
WO  2015087285 A1  6/2015

OTHER PUBLICATIONS

European Patent Office; Communication issued in app. No. 17830615.5 dated Feb. 23, 2022.

(Continued)

*Primary Examiner* — Eduardo C Robert
*Assistant Examiner* — Michelle C Eckman
(74) *Attorney, Agent, or Firm* — Dinsmore & Shohl LLP

(57) ABSTRACT

An expandable implant (100, 150, 160, 200, 250, 300, 400) has a base (10) and a displaceable element (12) hingedly interconnected at one end. At the other end, the base and the displaceable element are formed with complementary jaws (24, 26) which provide continuous overlap of facing surfaces over a range of angular positions of the displaceable element relative to said base. In some cases, the first end portion (16) of the displaceable element (12) is formed with projecting teeth (28) forming a partial gear centered on an axis (18) of the hinged interconnection with the base (12) for engaging a worm gear. In certain embodiments, the base is formed with a socket (30) for removably receiving a worm gear tool (32) for engaging the teeth (28) and displacing said displaceable element. After expansion, the worm-gear tool (32) can be removed.

15 Claims, 21 Drawing Sheets

Related U.S. Application Data

(60) Provisional application No. 62/364,885, filed on Jul. 21, 2016.

(52) U.S. Cl.
CPC ........ A61F 2002/3052 (2013.01); A61F 2002/3054 (2013.01); A61F 2002/3055 (2013.01); A61F 2002/30156 (2013.01); A61F 2002/30261 (2013.01); A61F 2002/30266 (2013.01); A61F 2002/30471 (2013.01); A61F 2002/30523 (2013.01); A61F 2002/30538 (2013.01); A61F 2002/30593 (2013.01); A61F 2002/30904 (2013.01); A61F 2002/4627 (2013.01)

(56) References Cited

U.S. PATENT DOCUMENTS

| | | |
|---|---|---|
| 6,193,757 B1 * | 2/2001 | Foley ............ A61F 2/4455 623/17.16 |
| 6,436,140 B1 | 8/2002 | Liu |
| 6,443,989 B1 | 9/2002 | Jackson |
| 6,685,742 B1 | 2/2004 | Jackson |
| 6,962,606 B2 | 11/2005 | Michelson |
| 7,641,690 B2 | 1/2010 | Abdou |
| 7,763,028 B2 | 7/2010 | Lim |
| 8,187,332 B2 | 5/2012 | McLuen |
| 8,486,149 B2 | 7/2013 | Saidha |
| 9,278,008 B2 | 3/2016 | Perloff et al. |
| 9,439,771 B2 | 9/2016 | Packer |
| 9,498,347 B2 | 11/2016 | McLean |
| 9,795,493 B1 | 10/2017 | Bannigan |
| 9,801,734 B1 | 10/2017 | Stein |
| 9,962,272 B1 | 5/2018 | Daffinson |
| 10,105,238 B2 | 10/2018 | Koch |
| 10,195,524 B2 | 2/2019 | DeRidder |
| 10,426,634 B1 | 10/2019 | Al-Jazaeri |
| 10,786,367 B2 * | 9/2020 | Sharabani ............ A61F 2/447 |
| 2002/0128713 A1 * | 9/2002 | Ferree ............ A61F 2/4465 623/17.11 |
| 2003/0208275 A1 | 11/2003 | Michelson |
| 2004/0044411 A1 * | 3/2004 | Suddaby ............ A61F 2/4455 623/17.15 |
| 2004/0127994 A1 | 7/2004 | Kast |
| 2004/0162618 A1 | 8/2004 | Mujwid |
| 2005/0113916 A1 | 5/2005 | Branch |
| 2006/0030942 A1 | 2/2006 | Peterman |
| 2006/0030943 A1 * | 2/2006 | Peterman ............ A61F 2/447 623/17.11 |
| 2006/0206207 A1 | 9/2006 | Dryer |
| 2011/0172774 A1 | 7/2011 | Varela |
| 2012/0029636 A1 | 2/2012 | Ragab |
| 2012/0029637 A1 | 2/2012 | Ragab |
| 2012/0185049 A1 | 7/2012 | Varela |
| 2012/0271422 A1 | 10/2012 | Miller |
| 2013/0041471 A1 | 2/2013 | Siegal |
| 2013/0079883 A1 | 3/2013 | Butler |
| 2013/0158664 A1 | 6/2013 | Palmatier |
| 2013/0274883 A1 | 10/2013 | McLuen |
| 2014/0114420 A1 * | 4/2014 | Robinson ............ A61F 2/447 623/17.16 |
| 2014/0188224 A1 | 7/2014 | Dmuschewsky |
| 2014/0249629 A1 | 9/2014 | Moskowitz |
| 2014/0277508 A1 | 9/2014 | Baynham |
| 2014/0288653 A1 | 9/2014 | Chen |
| 2014/0309741 A1 | 10/2014 | Ganter |
| 2014/0343678 A1 * | 11/2014 | Suddaby ............ A61F 2/4611 623/17.16 |
| 2015/0012098 A1 | 1/2015 | Eastlack |
| 2015/0057755 A1 | 2/2015 | Suddaby |
| 2015/0066145 A1 | 3/2015 | Rogers |
| 2015/0148908 A1 | 5/2015 | Marino |
| 2015/0223945 A1 | 8/2015 | Weiman |
| 2015/0223946 A1 | 8/2015 | Weiman |
| 2015/0351925 A1 | 12/2015 | Emerick |
| 2016/0015522 A1 | 1/2016 | Amin |
| 2016/0022434 A1 | 1/2016 | Robinson |
| 2016/0030190 A1 | 2/2016 | Robinson |
| 2016/0038305 A1 | 2/2016 | Weiman |
| 2016/0089247 A1 | 3/2016 | Nichols |
| 2016/0100951 A1 * | 4/2016 | Suddaby ............ A61F 2/4455 623/17.16 |
| 2016/0113776 A1 | 4/2016 | Capote |
| 2016/0166396 A1 | 6/2016 | McClintock |
| 2016/0206440 A1 | 7/2016 | DeRidder |
| 2016/0250034 A1 | 9/2016 | Loebl |
| 2016/0324654 A1 * | 11/2016 | Loebl ............ A61F 2/4425 |
| 2016/0338846 A1 | 11/2016 | Walker |
| 2016/0354211 A1 | 12/2016 | Packer |
| 2017/0042695 A1 | 2/2017 | Foley |
| 2017/0100255 A1 | 4/2017 | Hleihil |
| 2017/0105844 A1 | 4/2017 | Kuyler |
| 2017/0112631 A1 | 4/2017 | Kuyler |
| 2017/0119538 A1 | 5/2017 | Baynham |
| 2017/0128228 A1 | 5/2017 | Goel |
| 2017/0151066 A1 | 6/2017 | Thibodeau |
| 2017/0156885 A1 | 6/2017 | Zur |
| 2017/0172758 A1 | 6/2017 | Field |
| 2017/0181863 A1 | 6/2017 | Bjork |
| 2017/0189200 A1 | 7/2017 | Miller |
| 2017/0209282 A1 | 7/2017 | Aghayev |
| 2017/0216045 A1 | 8/2017 | Dewey |
| 2017/0231780 A1 | 8/2017 | D'Urso |
| 2017/0246006 A1 | 8/2017 | Carnes |
| 2017/0296352 A1 | 10/2017 | Richerme |
| 2017/0304071 A1 | 10/2017 | Black |
| 2017/0312090 A1 | 11/2017 | Sharabani |
| 2017/0312092 A1 | 11/2017 | Link |
| 2017/0319352 A1 | 11/2017 | Dewey |
| 2017/0325967 A1 | 11/2017 | Link |
| 2017/0333198 A1 | 11/2017 | Robinson |
| 2017/0333199 A1 | 11/2017 | Sharifi-Mehr |
| 2017/0333200 A1 | 11/2017 | Amin |
| 2017/0367842 A1 | 12/2017 | Predick |
| 2017/0367843 A1 | 12/2017 | Eisen |
| 2017/0367845 A1 | 12/2017 | Eisen |
| 2018/0000606 A1 | 1/2018 | Hessler |
| 2018/0000609 A1 | 1/2018 | Hessler |
| 2018/0014947 A1 | 1/2018 | Baynhahm |
| 2018/0036137 A1 | 2/2018 | Levieux |
| 2018/0036138 A1 | 2/2018 | Robinson |
| 2018/0104066 A1 | 4/2018 | Bae |
| 2018/0116815 A1 | 5/2018 | Kuyler |
| 2018/0125671 A1 | 5/2018 | Bernard |
| 2018/0147066 A1 | 5/2018 | Daffinson |
| 2018/0185164 A1 | 7/2018 | Sharabani |
| 2018/0193164 A1 | 7/2018 | Shoshtaev |
| 2018/0289499 A1 | 10/2018 | Robinson |
| 2018/0303621 A1 | 10/2018 | Brotman |
| 2018/0344473 A1 | 12/2018 | Baynham |
| 2018/0360616 A1 | 12/2018 | Luu |
| 2019/0000644 A1 * | 1/2019 | Moore ............ A61F 2/4465 |
| 2019/0021868 A1 | 1/2019 | Ludwig |
| 2019/0021871 A1 | 1/2019 | Baynham |
| 2019/0053912 A1 | 2/2019 | Suddaby |
| 2019/0083279 A1 | 3/2019 | Suddaby |
| 2019/0110900 A1 | 4/2019 | Suddaby |
| 2019/0133779 A1 | 5/2019 | McLaughlin |
| 2019/0133782 A1 | 5/2019 | McLaughlin |
| 2019/0151111 A1 | 5/2019 | Dewey |
| 2019/0175357 A1 | 6/2019 | Sharabani |
| 2019/0201210 A1 | 7/2019 | Besaw |
| 2019/0254836 A1 | 8/2019 | Cowan |
| 2019/0254838 A1 | 8/2019 | Miller |
| 2019/0274836 A1 | 9/2019 | Eisen |
| 2019/0282373 A1 | 9/2019 | Alheidt |
| 2019/0298524 A1 | 10/2019 | Lauf |

(56) References Cited

U.S. PATENT DOCUMENTS

2019/0307577 A1 10/2019 Predick
2020/0008951 A1 1/2020 McClintock

OTHER PUBLICATIONS

European Patent Office; Extended European Search Report for App. No. 17830615.5 dated Feb. 5, 2020, 7 pages.
Israel Patent Office, International Search Report and Written Opinion for PCT/IL2017/050828 dated Oct. 24, 2017, 8 pages.

* cited by examiner

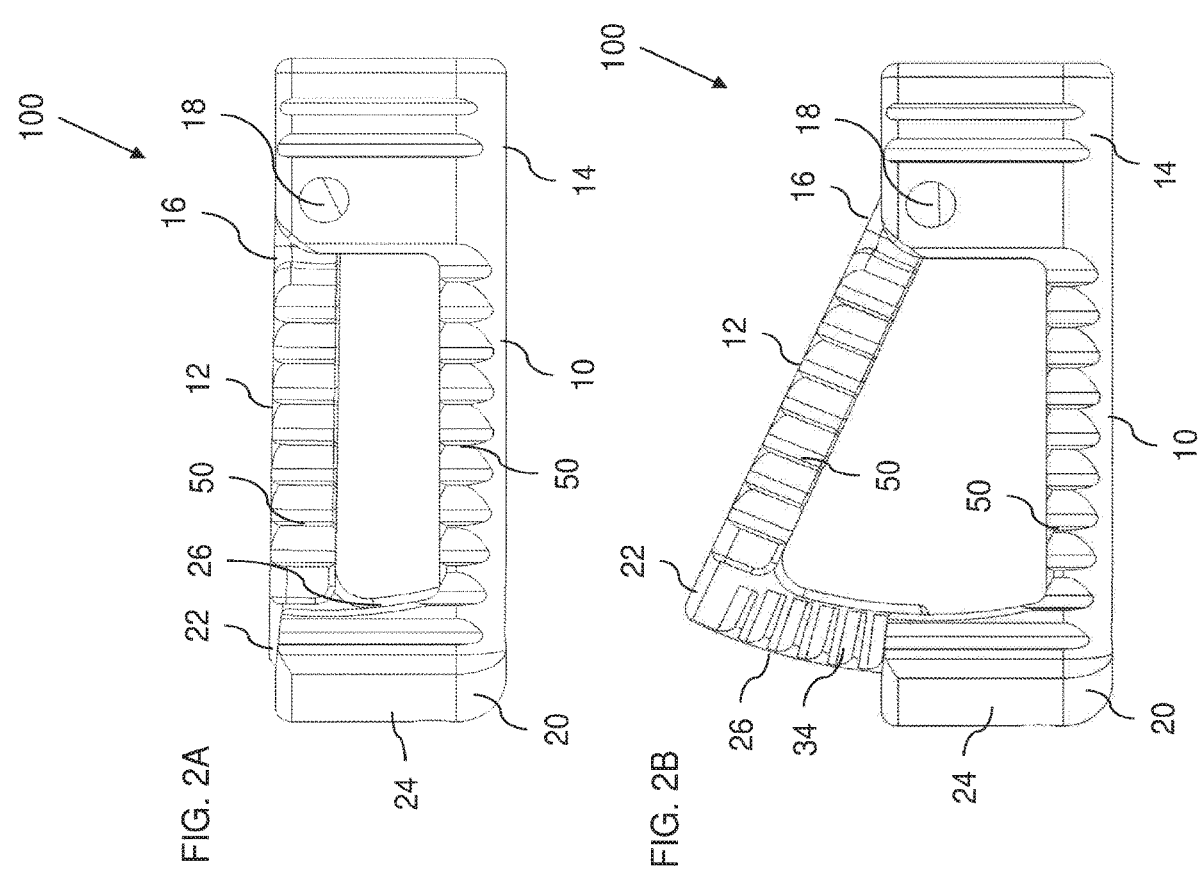

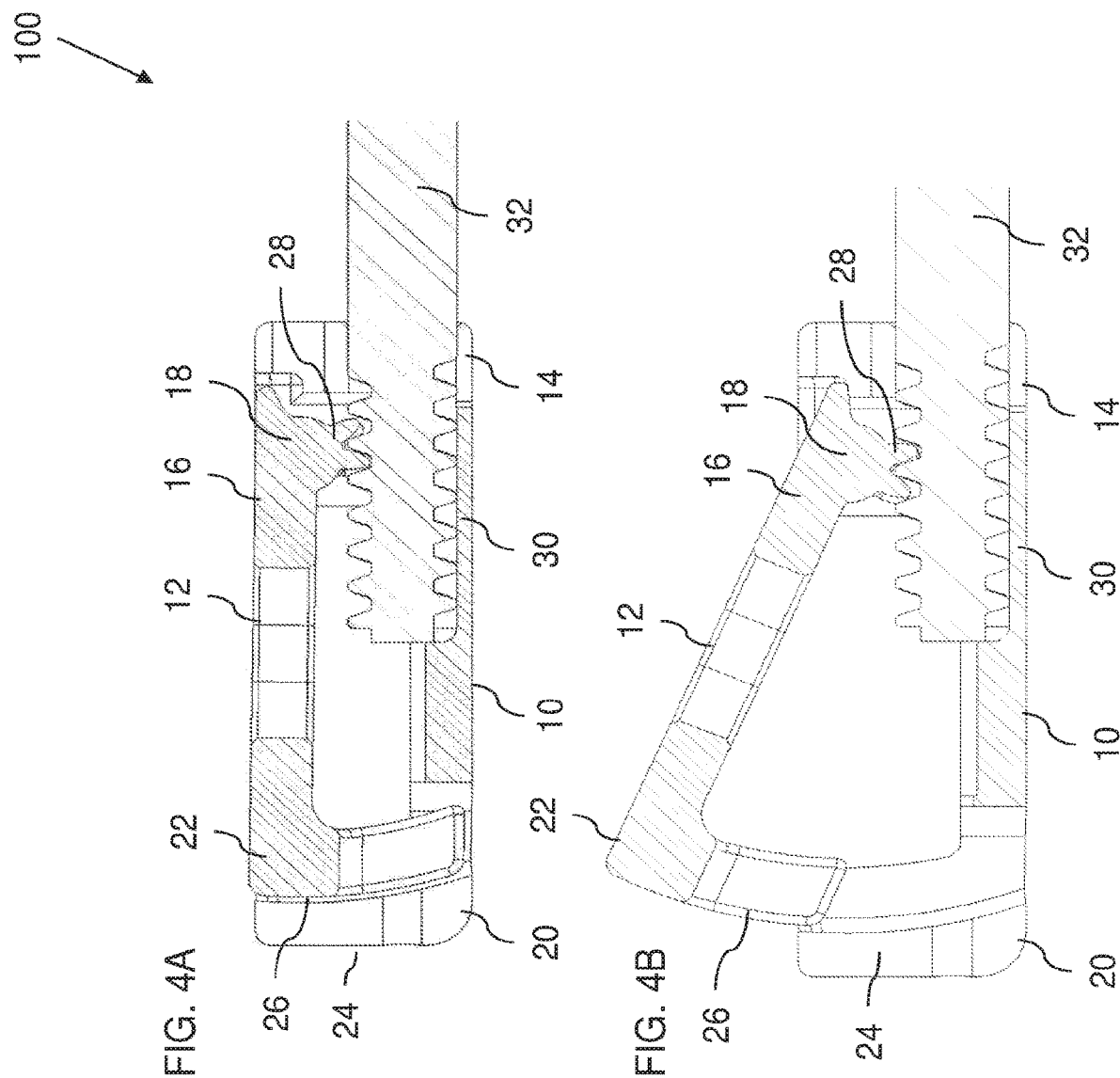

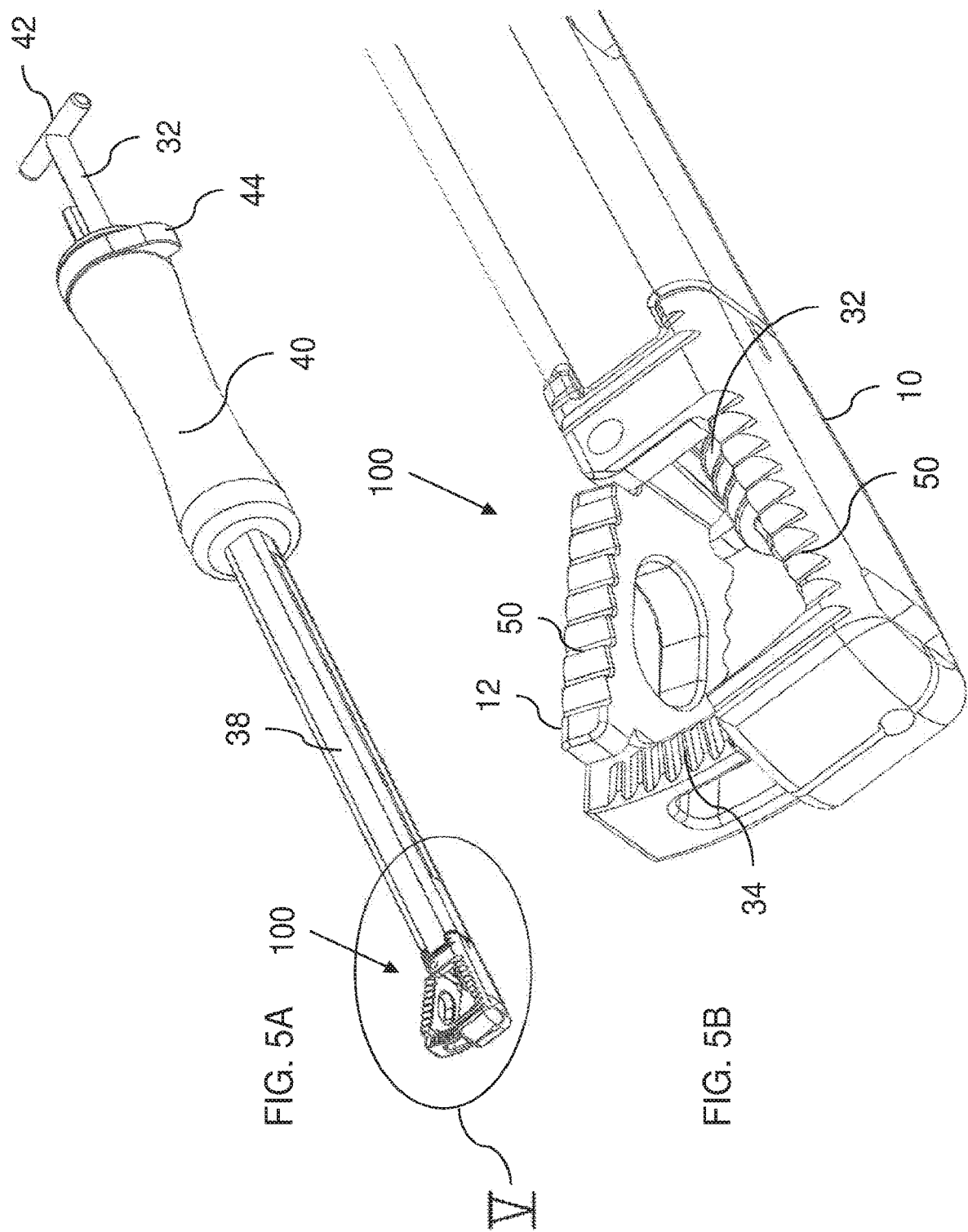

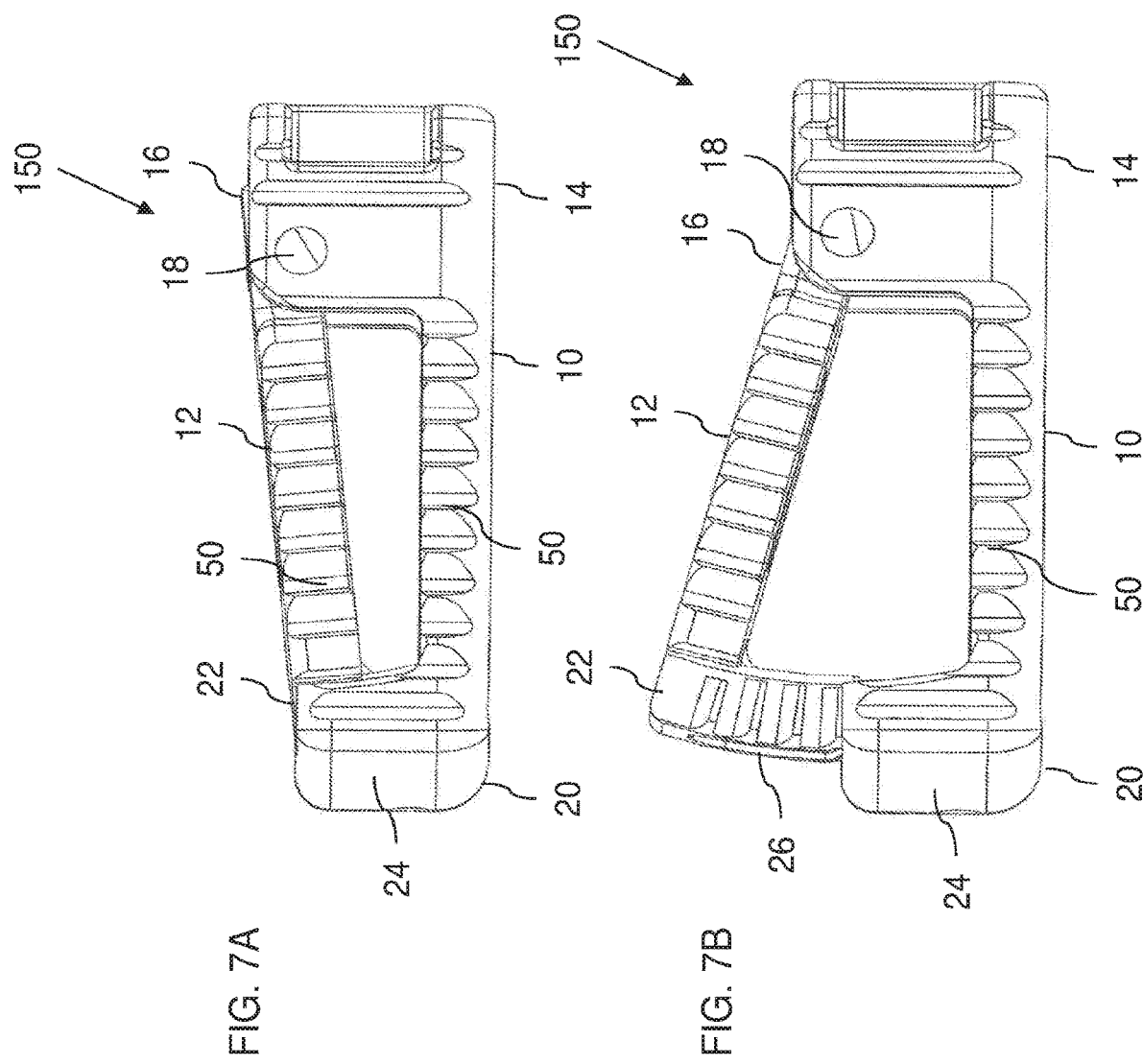

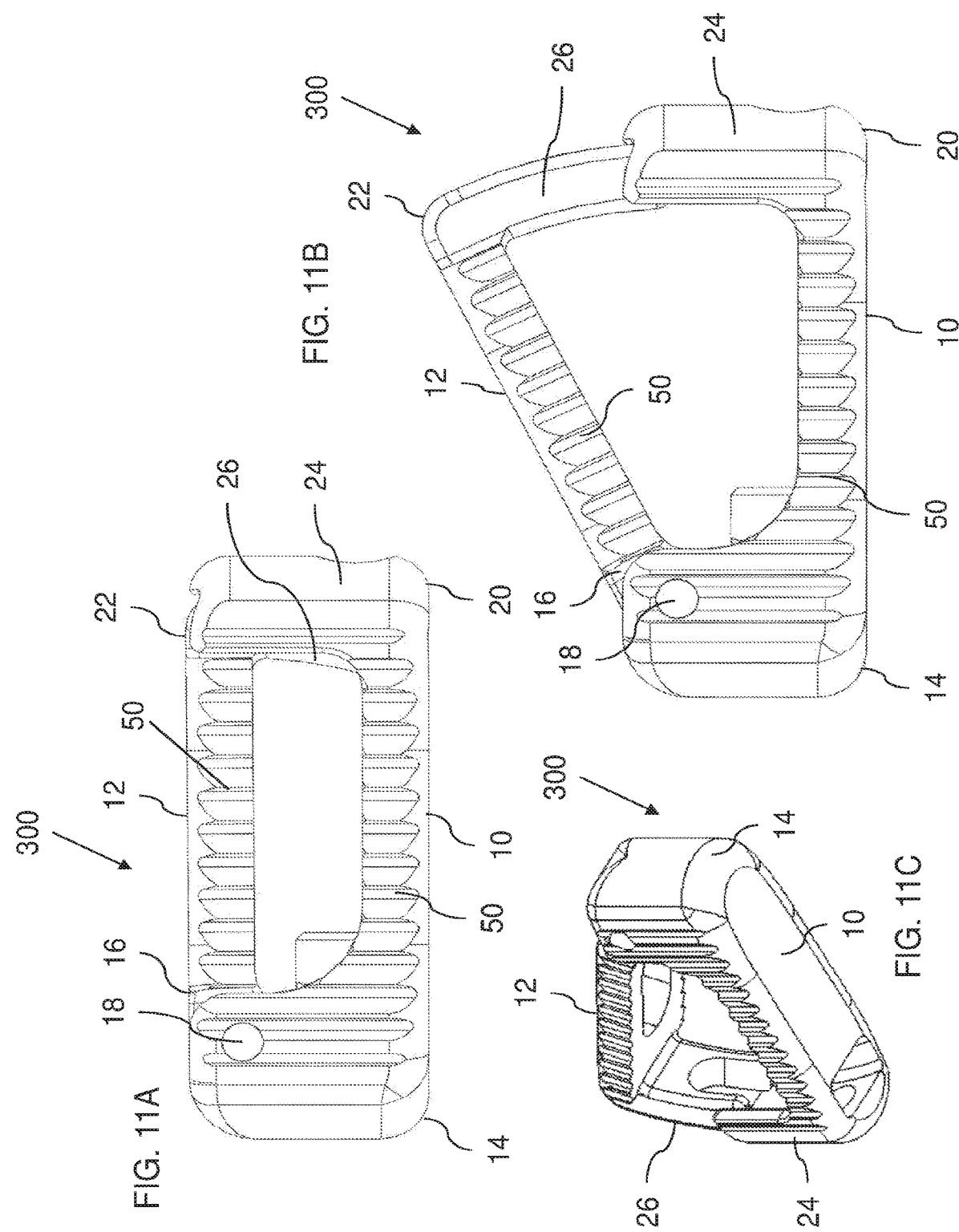

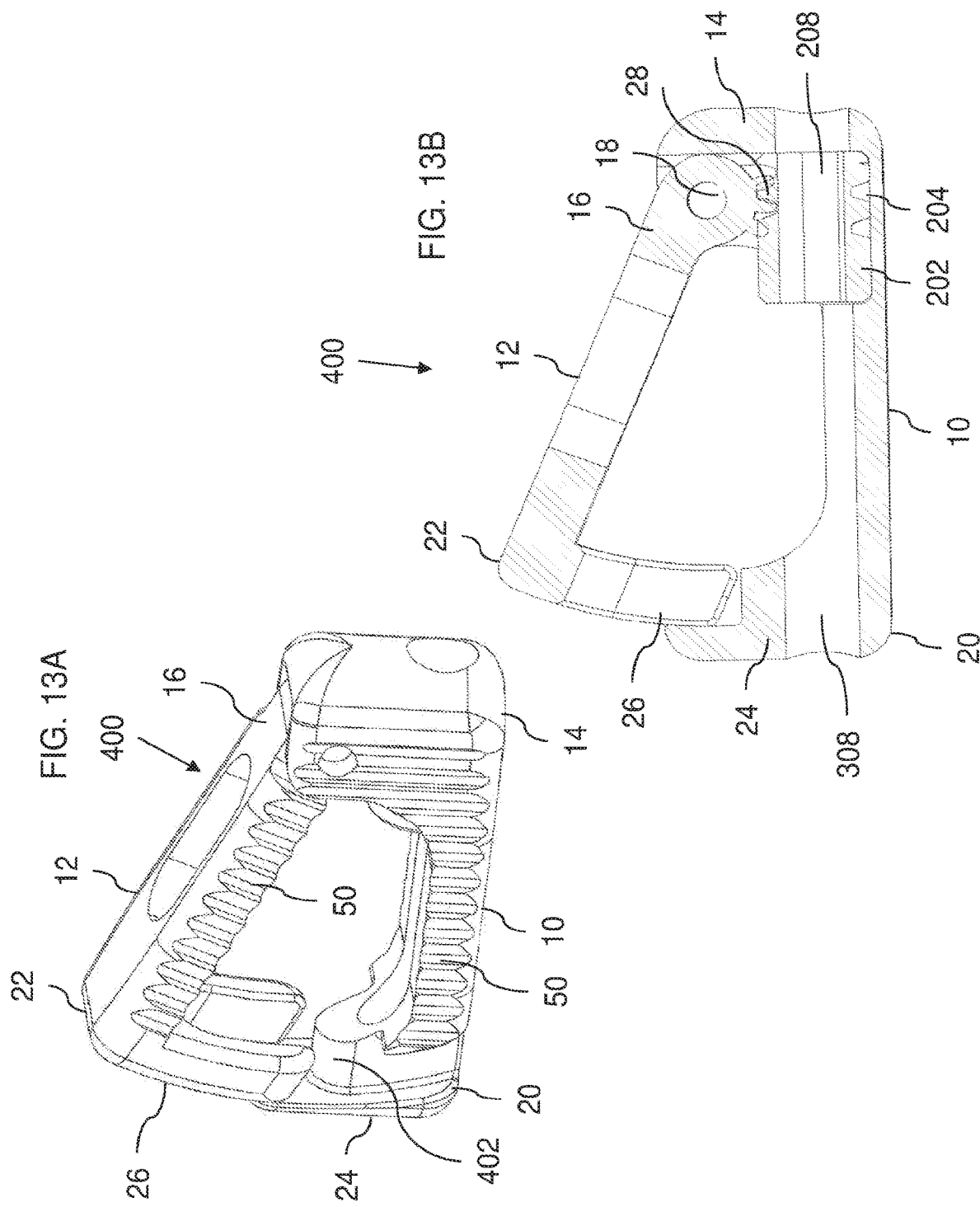

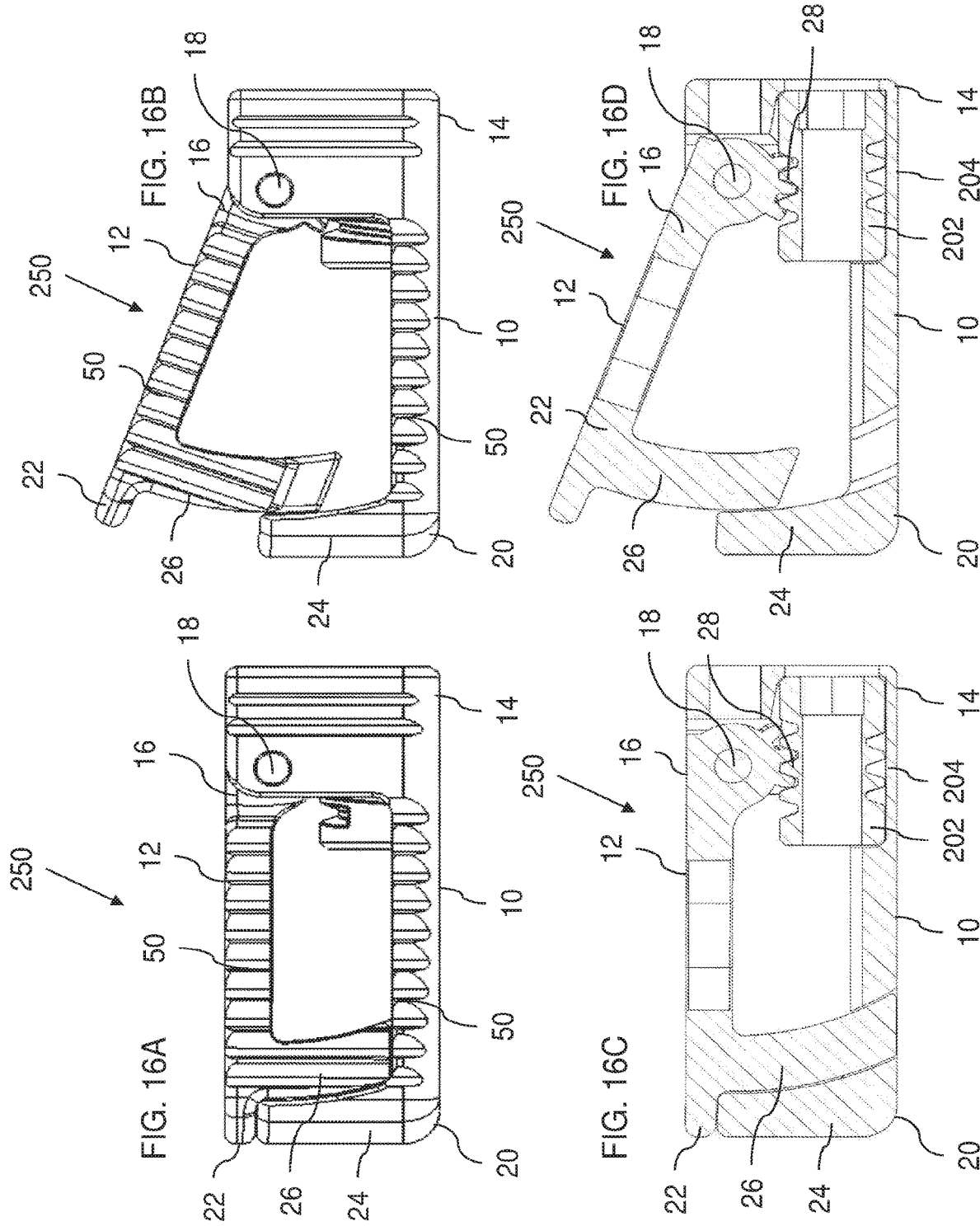

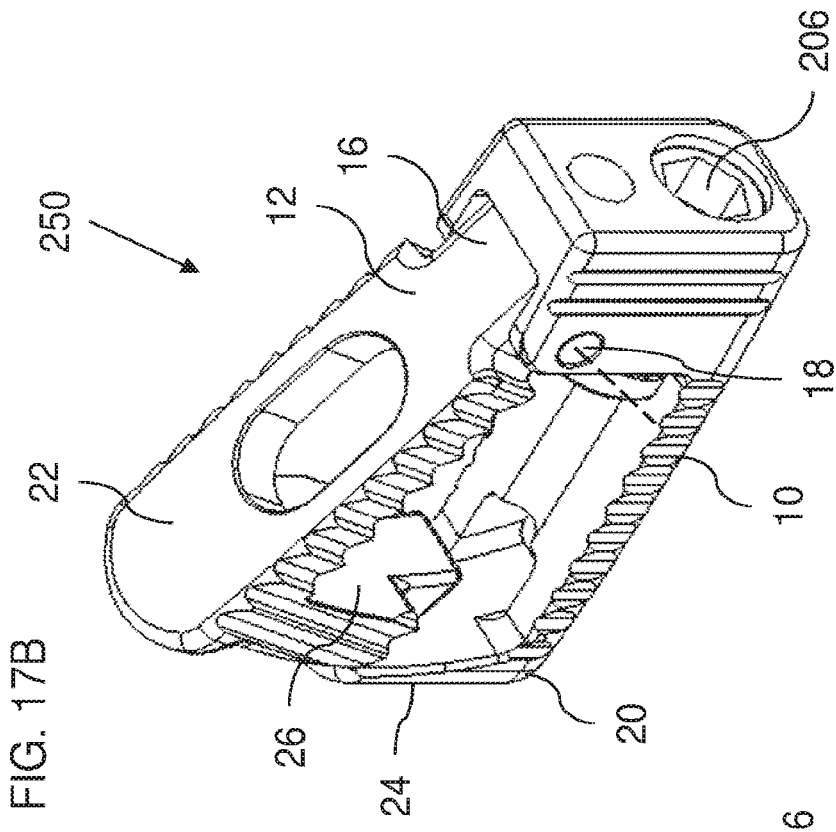
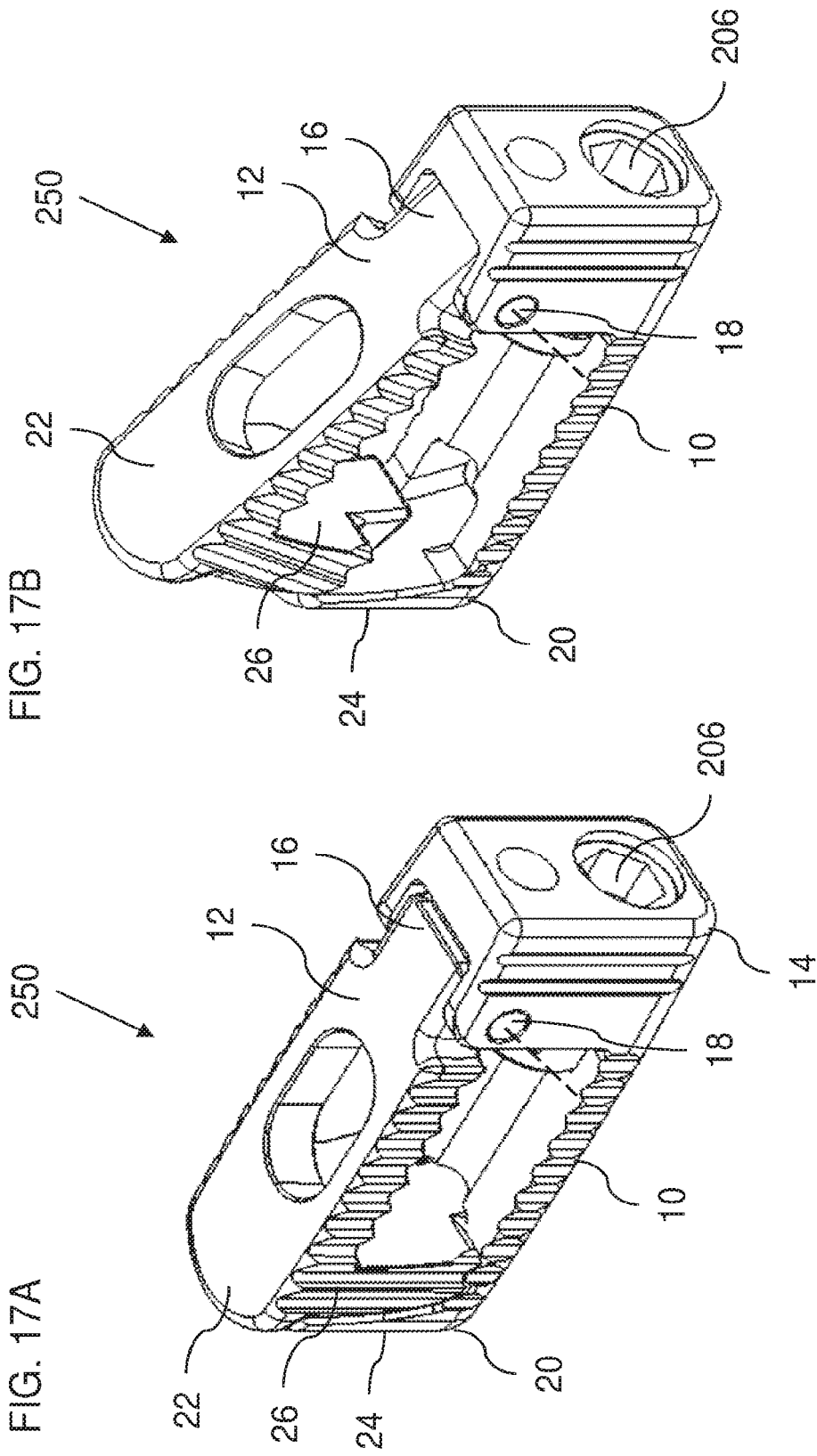
FIG. 17A
FIG. 17B

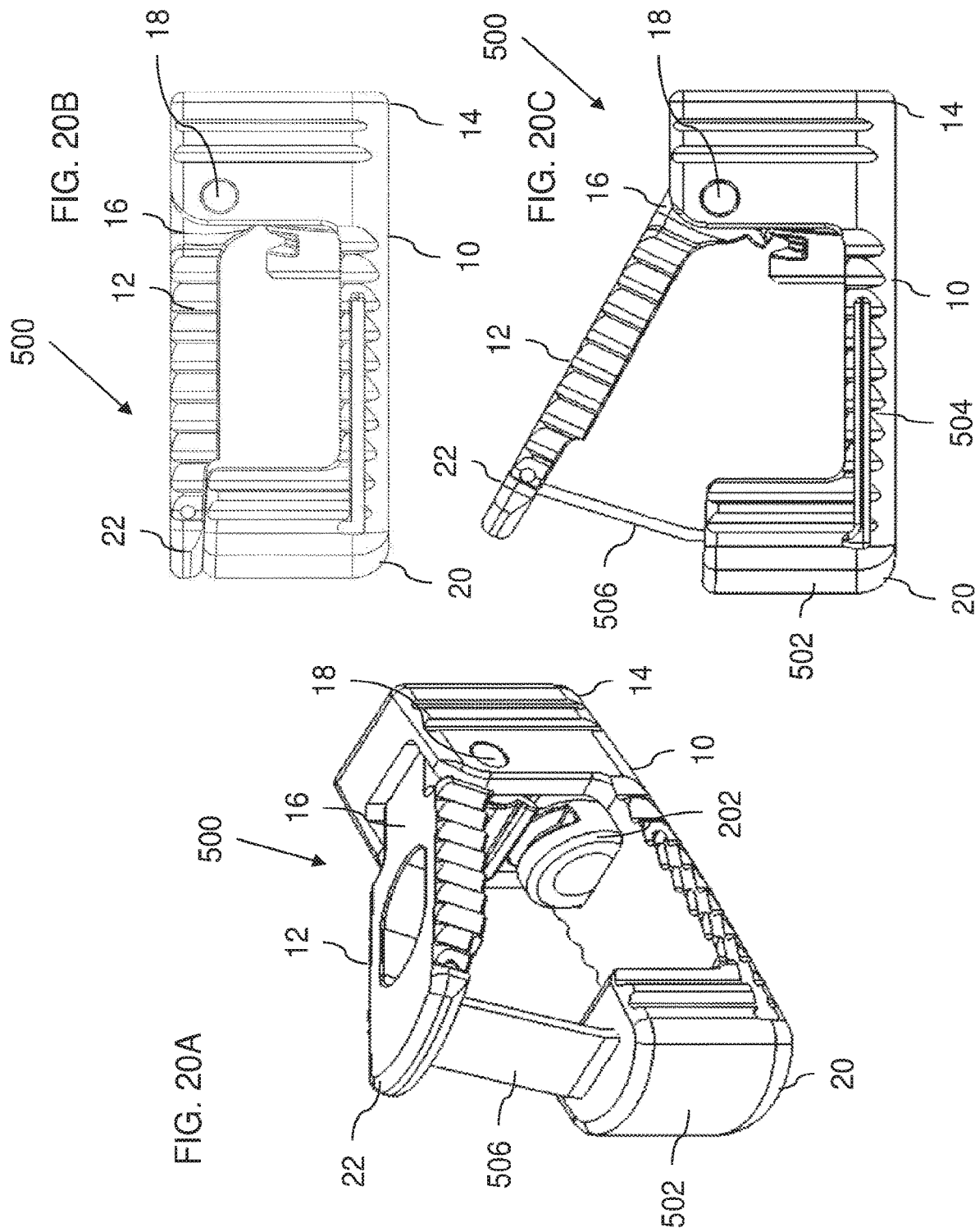

EXPANDABLE IMPLANT

FIELD AND BACKGROUND OF THE INVENTION

The present invention relates to expandable implants and, in particular, it concerns an implant formed primarily from two hingedly-connected elements which maintains an enclosed internal volume as it expands.

In the field of minimally invasive spinal surgery (MISS), it is known to employ various implants which assume a compact form for insertion via a small incision into the body, and then expand to assume a larger deployed state within the body.

Many expandable implants have relatively complex mechanisms, including numerous moving parts which must be assembled carefully, potentially leading to increased costs and/or reduced reliability. Complex designs also pose particular challenges for surgical approaches which require a high degree of miniaturization.

Simpler designs, on the other hand, may fail to define a closed shape suitable for filling with filling material.

SUMMARY OF THE INVENTION

The present invention is an expandable implant.

According to the teachings of an embodiment of the present invention there is provided, an expandable implant comprising: (a) a base extending from a first end portion to a second end portion; and (b) a displaceable element extending from a first end portion to a second end portion, wherein the first end portions of the base and the displaceable element are hingedly interconnected, and wherein the second end portions of the base and the displaceable element are formed with complementary jaws, the complementary jaws being configured to provide continuous overlap over a range of angular positions of the displaceable element relative to the base.

According to a further feature of an embodiment of the present invention, the complementary jaws provide complementary facing arcuate surfaces.

According to a further feature of an embodiment of the present invention, the complementary jaws provide complementary facing surfaces corresponding to solids of revolution about an axis of the hinged interconnection.

According to a further feature of an embodiment of the present invention, a first jaw of the complementary jaws comprises at least one projecting portion that is interposed between inward facing surfaces of a second of the complementary jaws.

According to a further feature of an embodiment of the present invention, the inward facing surfaces are integrated with an end wall such that the inward facing surfaces and the end wall encompass the at least one projecting portion on three sides.

According to a further feature of an embodiment of the present invention, the complementary jaws are configured to provide the continuous overlap over a range of angular positions of the displaceable element relative to the base spanning at least 10 degrees, and in some preferred cases at least 20 degrees.

According to a further feature of an embodiment of the present invention, the first end portion of the displaceable element is formed with a plurality of projecting teeth configured as a partial gear centered on an axis of the hinged interconnection with the base, the projecting teeth being configured for engaging a worm gear.

According to a further feature of an embodiment of the present invention, the first end portion of the base is formed with a socket configured for removably receiving a worm gear tool for engaging the teeth and displacing the displaceable element.

According to a further feature of an embodiment of the present invention, the displaceable element is displaceable relative to the base from an initial position defining a compact configuration of the expandable implant towards a deployed position defining an expanded configuration of the expandable implant, and wherein the complementary jaws are formed with complementary parts of a retention configuration configured for inhibiting return of the displaceable element towards the initial position.

According to a further feature of an embodiment of the present invention, the retention configuration comprises at least one sequence of ratchet teeth deployed to inhibit return of the displaceable element from a range of positions of the displaceable element towards the initial position.

According to a further feature of an embodiment of the present invention, the retention configuration comprises two resilient retention elements separated by a slot, and wherein the retention configuration is configured such that, on insertion of a prising tool into the slot to increase a spacing of the slot, the retention configuration is released to allow displacement of the displaceable element towards the initial position.

According to a further feature of an embodiment of the present invention, there is also provided a worm gear rotatably deployed within the first end portion of the base in engagement with the teeth such that rotation of the worm gear effects displacement of the displaceable element, wherein the worm gear is a hollow worm gear formed with an axial through-bore for introduction of filling material via the axial through-bore into the expandable implant.

According to a further feature of an embodiment of the present invention, the second end portion of the base is formed with an aperture aligned with the worm gear so as to allow insertion of a tool through the aperture to engage the worm gear for rotating the worm gear.

According to a further feature of an embodiment of the present invention, there is also provided a worm gear rotatably deployed within the first end portion of the base in engagement with the teeth such that rotation of the worm gear effects displacement of the displaceable element, and wherein the second end portion of the base is formed with an aperture aligned with the worm gear so as to allow insertion of a tool through the aperture to engage the worm gear for rotating the worm gear.

There is also provided according to the teachings of an embodiment of the present invention, an expandable implant comprising: (a) a base extending from a first end portion to a second end portion; and (b) a displaceable element extending from a first end portion to a second end portion, wherein the first end portions of the base and the displaceable element are hingedly interconnected, and wherein the first end portion of the displaceable element is formed with a plurality of projecting teeth configured as a partial gear centered on an axis of the hinged interconnection with the base, the projecting teeth being configured for engaging a worm gear, and wherein the first end portion of the base is formed with a socket configured for removably receiving a worm gear tool for engaging the teeth and displacing the displaceable element.

BRIEF DESCRIPTION OF THE DRAWINGS

The invention is herein described, by way of example only, with reference to the accompanying drawings, wherein:

FIGS. 2A and 2B are side views of the implant of FIG. 1A shown in an initial closed state and an expanded state, respectively;

FIGS. 4A and 4B are cross-sectional views taken along a central longitudinal plane through the implant of FIG. 1A, the implant being shown with the worm-gear tool inserted, with the implant shown in its initial closed state and its expanded state, respectively;

FIG. 5A is an isometric view of the implant of FIG. 1A attached to a delivery system;

FIG. 5B is an enlarged view of the region of FIG. 5A designated V;

FIGS. 7A and 7B are side views of a variant implementation of the implant of FIG. 1A, shown in an initial closed state and an expanded state, respectively;

FIGS. 11A and 11B are side views of the implant of FIG. 10A shown in an initial closed state and an expanded state, respectively;

FIG. 11C is a bottom isometric view of the implant of FIG. 10A;

FIG. 13A is an isometric view of an expandable implant, constructed and operative according to a further embodiment of the present invention, shown in an expanded state;

FIG. 13B is a cross-sectional view taken along a central longitudinal plane of FIG. 13A;

FIGS. 16A and 16B are side views of an expandable implant, constructed and operative according to a further embodiment of the present invention, shown in an initial closed state and an expanded state, respectively;

FIGS. 16C and 16D are cross-sectional views taken along a central longitudinal plane of FIGS. 16A and 16B, respectively;

FIGS. 17A and 17B are isometric views of the expandable implant of FIGS. 16A and 16B, respectively;

FIG. 20A is an isometric view of an expandable implant, constructed and operative according to a further embodiment of the present invention, shown in an expanded state;

FIGS. 20B and 20C are side views of the implant of FIG. 20A shown in an initial closed state and an expanded state, respectively.

DESCRIPTION OF THE PREFERRED EMBODIMENTS

Figure 1A:
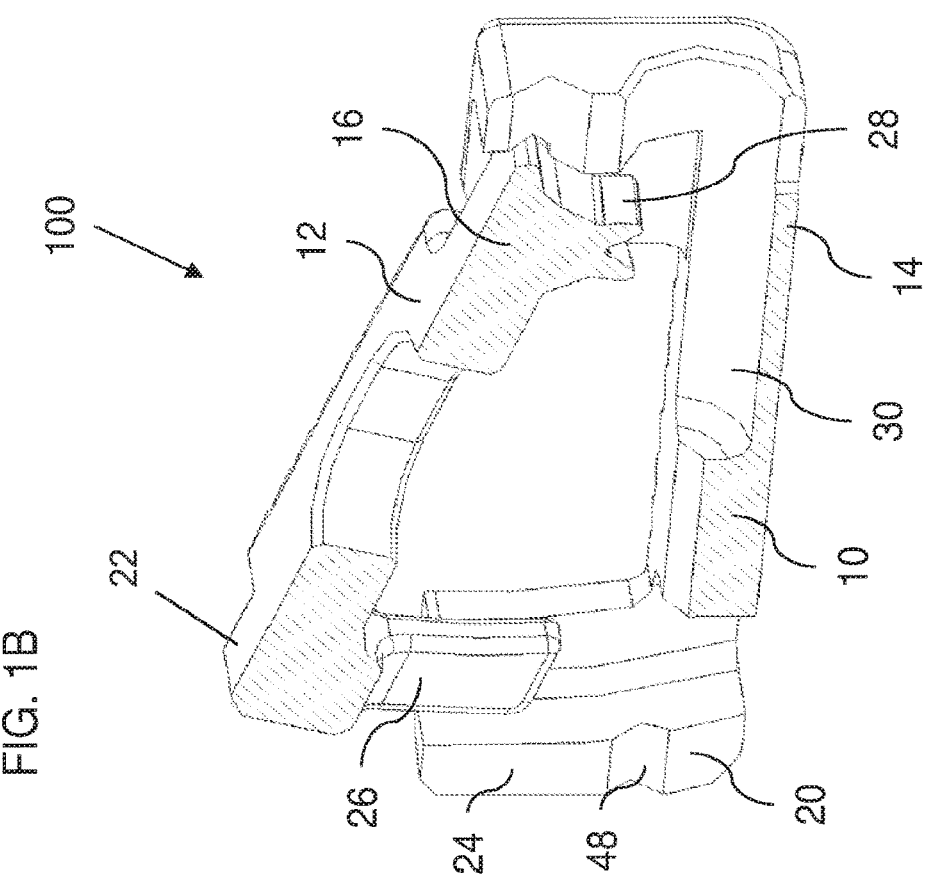
FIG. 1A is an isometric view of an expandable implant, constructed and operative according to an embodiment of the present invention, shown in an expanded state.
Figure 1B:
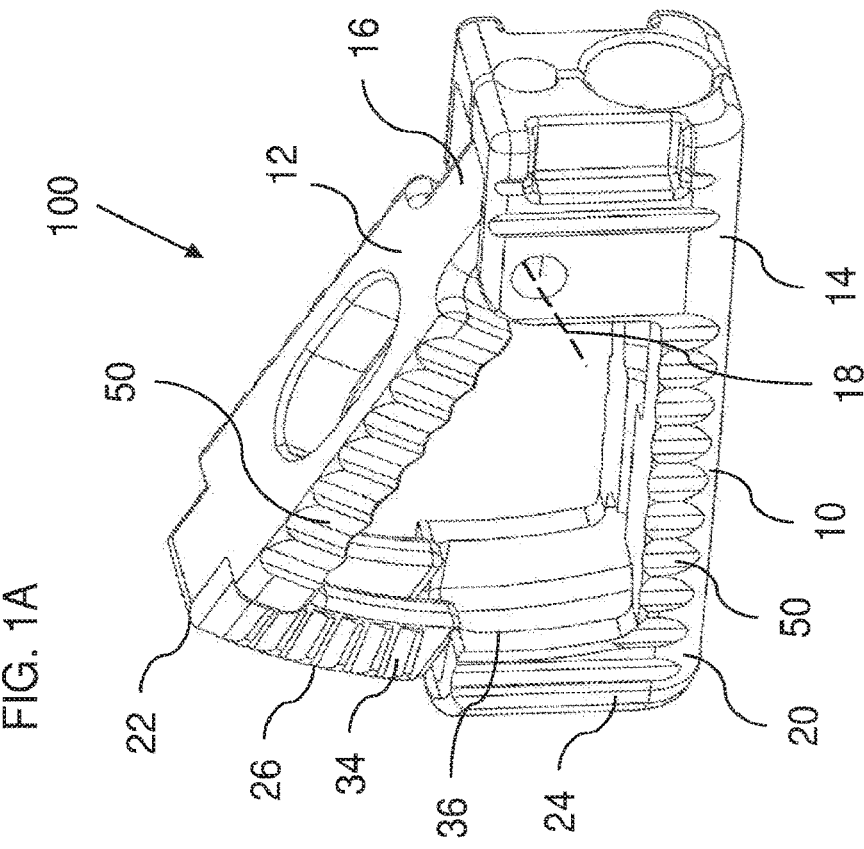
FIG. 1B is a cut-away isometric view similar to FIG. 1A cut along a central longitudinal plane.

The present invention is an expandable implant.

The principles and operation of expandable implants according to the present invention may be better understood with reference to the drawings and the accompanying description.

Referring now to the drawings, the present invention will be illustrated herein with reference to a number of exemplary embodiments, principally including a first embodiment illustrated in FIGS. 1A-6C, a second embodiment illustrated in FIGS. 8A-9B, a third embodiment illustrated in FIGS. 10A-12B, and a fourth embodiment illustrated in FIGS. 13A-15B. The remaining figures relate to a number of variant implementations and alternative embodiments that will be addressed separately below.

Referring first generically to the above four embodiments, certain preferred embodiments of the present invention provide an expandable implant, generally designated 100, 200, 300 and 400, respectively. Analogous features of the different embodiments will be referred to by the same reference numeral throughout the drawings. In each case, the expandable implant includes a base 10 and a displaceable element 12. A first end portion 14 of base 10 is hingedly interconnected to a first end portion 16 of displaceable element 12 so as to be pivotable about an axis 18. Second end portions 20 and 22 of base 10 and displaceable element 12 are formed with complementary jaws 24 and 26, respectively. According to certain particularly preferred embodiments of the present invention, the complementary jaws are configured to provide continuous overlap over a range of angular positions of the displaceable element relative to the base. The particular range of angular positions accommodated by the implant while maintaining overlap depends upon the intended application, as will be discussed further below, but in most cases will be in excess of 10 degrees, and in many cases in excess of 20 degrees.

By providing complementary jaws as disclosed herein, it is possible to provide a particularly simple implant design, with as few as two primary structural components hinged together at a single pivotal connection, which allows considerable expansion of the implant after delivery into the body, while maintaining an enclosed volume within the implant for containing filling material.

It will be useful to define certain terminology as used herein in the description and claims. The present invention relates to an "implant". The term implant is used herein in the description and claims to refer to any implant useful for introducing into a human or animal body, particularly as part of an orthopedic surgical procedure. The invention will be exemplified herein with reference specifically to the field of spinal surgery, and in particular, in applications in which the implant is deployed in the intervertebral space. However, the implant of the present invention is not limited to such applications, and may find utility in a range of other spinal and non-spinal procedures. The phrase "expandable implant" refers to an implant which can be expanded once within the body so as to increase its external dimensions in at least one direction.

Where reference is made to an "enclosed volume", this refers to a volume which lies within a closed loop formed by an implant, preferably so that the volume is encompassed on all sides sufficiently to form a barrier tending to prevent, or at least limit, dispersion of various types of filling material. The enclosure is typically a two-dimensional enclosure, meaning that the volume defined by the implant is effectively enclosed in a plane of a loop formed by the implant, but is open in a direction perpendicular to that plane. In applications in which the implant is deployed between inward-facing tissue surfaces, those tissue surfaces together with the structure of the implant cooperate to define a three-dimensional enclosure. The term "enclosed" does not rule out the presence of one or more openings or windows formed through one or more elements of the enclosing structure, which may for example define a preferred direction of controlled release of excess filling material for applications where such overflow is appropriate. Furthermore, the enclosing structure does not necessarily have a uniform wall height around the entire enclosure, and is still considered to "enclose" the volume so long as it is sufficient to limit dispersion of the filling material.

The structure of jaws 24 and 26 is referred to variously as providing "complementary facing arcuate surfaces" or "complementary facing surfaces corresponding to solids of revolution about axis 18". These phrases refer to various geometries of facing surfaces that allow the surfaces to maintain close proximity over a range of pivotal motion between base 10 and displaceable element 12. The surfaces preferably approximate closely to an "arcuate contact profile" shaped to maintain sliding contact as the two elements move through relative pivotal motion. However, in order to accommodate manufacturing tolerances, the elements are typically designed to have a small clearance, preferably of less than 1 millimeter, and typically of no more than 0.5 millimeter. It is expected that, under conditions of loading within the body, these facing surfaces may in fact come into contact, and serve to provide mechanical strength by limiting the strain deformation of the components relative to each other. The facing surfaces may be in various forms, including, but not limited to, partial-cylindrical surfaces centered on axis 18 and/or planar surfaces perpendicular to axis 18. Other forms of contact surface may also be used where the contact surfaces are parts of a male-female pair of solids of revolution about axis 18. A number of different examples will be shown in the examples below, and unless otherwise stated, are interchangeable between the various disclosed embodiments. It should also be noted that any reference to "abutment" between the surfaces does not require that contact occurs in the unstressed state of the implant, but rather that the corresponding facing surfaces maintain facing overlap over the range of motion.

The implants of the present invention may be implemented using any biocompatible material with suitable mechanical properties, including but not limited to various polymer materials, such as PEEK, ceramic materials, and various metals and metal alloys. Certain particularly preferred implementations are formed primarily, or exclusively, from titanium, which combines mechanical strength with good bone integration properties.

Referring still generically to expandable implants 100, 200, 300 and 400, in certain particularly preferred implementations of the present invention, an opening mechanism employed to expand the implant within the body is based on the principle of a worm gear engagement. Accordingly, in such embodiments, first end portion 16 of displaceable element 12 is formed with a plurality of projecting teeth 28 configured as a partial gear centered on axis 18. Projecting teeth 28 are configured for engaging a complementary worm gear.

Turning now specifically to the non-limiting example of expandable implant 100, this implementation employs a removable worm gear tool as part of the delivery system which is removed from the body after expansion of the implant. To this end, first end portion 14 of base 10 is formed with a socket 30 (FIG. 1B) configured for removably receiving a worm gear tool 32 (FIGS. 3, 4A and 4B) which engages teeth 28 in order to actuate expansion of the implant.

In order to maintain a deployed state of the implant when worm gear tool 32 is withdrawn, a locking or retention mechanism is preferably provided. A locking mechanism can be implemented in various ways. One particularly simple locking mechanism is the use of a tightenable clamping screw (not shown) mounted in first end portion 14 which bears on end portion 16 in the region of the pivotal connection and locks the desired relative positions of base 10 and displaceable element 12. However, in some cases, it is preferred to provide a retention mechanism which does not require separate actuation, and will retain whatever degree of expansion of the implant has been achieved.

In an alternative set of implementations, complementary jaws 24 and 26 are formed with complementary parts of a retention configuration configured for inhibiting return of displaceable element 12 after expansion towards an initial closed position. In the particularly preferred example illustrated here, the retention configuration is implemented as at least one sequence of ratchet teeth 34, here shown as part of jaws 26, that are deployed to inhibit return of the displaceable element from a range of positions of the displaceable element towards the initial position by engaging a facing lip 36 of jaws 24 (FIG. 1A).

In the particularly preferred non-limiting example illustrated here, ratchet teeth 34 and facing lip 36 are deployed on surfaces which are generally perpendicular to axis 18. As a result, in applications such as the laterally-expandable intervertebral cage detailed below with reference to FIGS. 6A-6C, load applied to the cage as a result of the normal axial loading between vertebrae tends to enhance locking of the ratchet engagement.

In the case illustrated here, jaw 26 is implemented as a pair of projecting portions that are interposed between inward facing surfaces of jaw 24. Jaw 26 could also be implemented as a single contiguous block (as in implant 200 below), except that it is desired to leave a central void to provide access for a ratchet release tool, as further detailed below. Additionally, jaw 24 is here implemented with an integrated end wall such that the inward facing surfaces and the end wall encompass the projecting portions of jaw 26 on three sides. Thus, in the closed state of the implant, the entire form of the distal tip of the implant is defined by second end portion 20 of base 10, while second end portion 22 of displaceable element 12 is essentially contained within end portion 20. This option may in some cases be advantageous as reducing interaction between the moveable element 12 and surrounding tissue during deployment, thereby minimizing frictional resistance to opening of the implant.

The hinged interconnection between base 10 and displaceable element 12 may be implemented using any suitable hinge engagement configuration. In the particularly preferred but non-limiting implementation best seen in FIG. 3, the engagement configuration is formed by pins 52 projecting bilaterally from the sides of first end portion 16 of the displaceable element which engage complementary sockets or apertures 54 in side walls of first end portion 14 of the base. In order to facilitate snapping together of the hinge structure, pins 52 may be formed with a chamfer 56 which helps to momentarily flex apart the sides of the base during assembly. A reversed configuration, in which pins projecting from the base engage recesses or a bore in the displaceable element may also be used. Alternatively, a separate hinge pin may be used.

The process of deployment of implant 100 will thus be understood as follows. With the implant in its initial closed state, it is attached to a hollow shaft 38 of a delivery system 40 via a suitable releasable gripping mechanism (not detailed here). Worm gear tool 32 is inserted through delivery system 40 and its handle 42 turned until the worm engages teeth 28 and advances to its fully inserted position, as illustrated in FIG. 4A. A locking mechanism 44 is then engaged to lock worm gear tool 32 against longitudinal motion relative to delivery system 40. Insertion of tool 32 can be performed either before or after insertion of the implant into the body.

Implant 100 is introduced via a suitable incision, after any required preparatory steps have been performed as is known in the art, so that the base is correctly positioned in the target location. Handle 42 is then rotated in a direction reversed relative to its insertion direction. Since worm gear tool 32 is locked by locking mechanism 44, the worm gear is unable to retract from the insert, and instead pushes against teeth 28, thereby forcing displaceable element 12 to rotate around axis 18, successively passing one after another of ratchet teeth 34 over lip 36. Optionally, worm gear tool 32 and teeth 28 may be configured with a left-handed threading direction, if a clockwise rotation is preferred as a more intuitive motion for expanding the implant.

Once a desired degree of expansion has been achieved, handle 42 is preferably turned slightly in the reverse direction, to remove loading from the worm gear. Locking mechanism 44 is then released, and worm gear tool 32 can be rotated until it disengages from teeth 28 and can be completely removed from the delivery system.

Figure 6A:
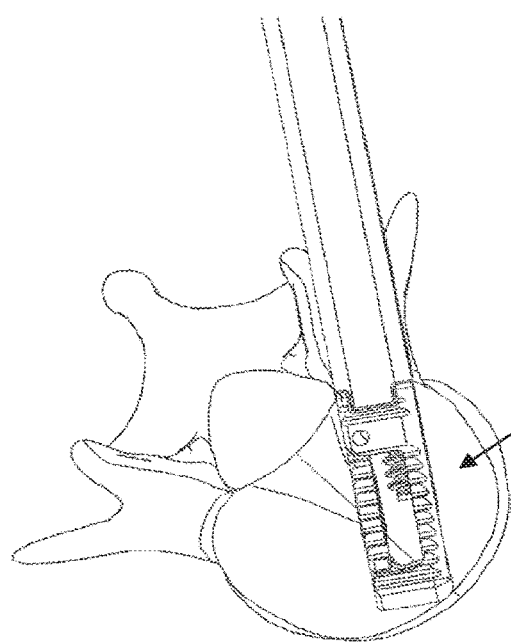
FIGS. 6A-6C are schematic plan views showing the positioning of the implant of FIG. 1A relative to a vertebra during deployment as a laterally-expandable intervertebral cage, the implant being shown in an initial compact state connected to a delivery system, in an expanded deployed state, and after filling and removal of the delivery system, respectively.
Figure 6B:
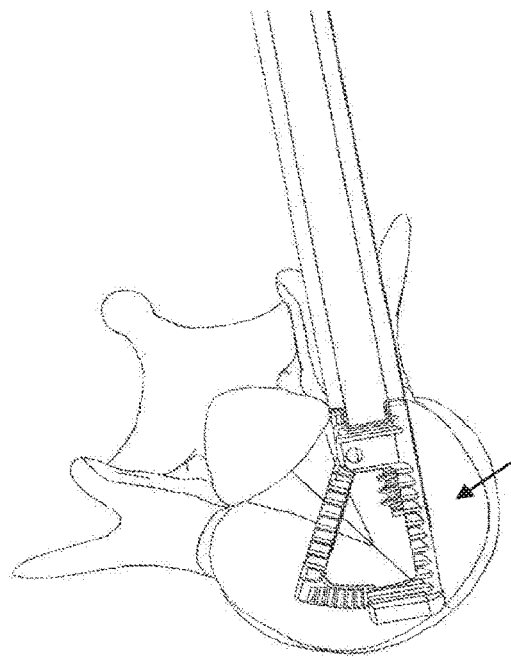

It will be noted that, after removal of worm gear tool 32, the lumen along which the worm gear tool was inserted and socket 30, together provide a relatively large access channel, facilitating introduction of filling material even for applications with small dimension access channels, such as TLIF or PLIF approaches. This removable worm-gear approach is believed to be of patentable significance independent of the aforementioned overlap of the jaws 24 and 26. FIGS. 6A and 6B illustrate the stages of operation as described above for a TLIF approach, and FIG. 6C illustrates the final deployed implant after filling and removal of the delivery system.

In some cases, it may be desired to reposition or remove the implant after deployment. In such cases, it may be necessary to collapse the implant back to its closed state. For this purpose, the retention mechanism is advantageously implemented so as to be selectively releasable. In the implementation shown here, jaw 24 is formed with a central slot 46, optionally intersecting with an additional aperture 48, which subdivides jaw 24 into two separate resilient elements, each bearing one of the ratchet-engaging lips 36. By insertion of a suitable prising tool, such as a screw-driver tip (not shown) into slot 46, it is possible to increase a spacing of the slot, moving lips 36 apart sufficiently to release the ratchet engagement and allow displacement of displaceable element 12 towards its initial position.

Notably, a particularly preferred implementation of expandable implant 100 typically consists essentially of only two primary structural components: base 10 and displaceable element 12, optionally with an additional hinge pin depending upon the chosen design for the hinge. The simplicity of the structure in turn results in reduced costs, increased reliability, and potentially greater miniaturization for applications in which compact dimensions are important.

Figure 3:
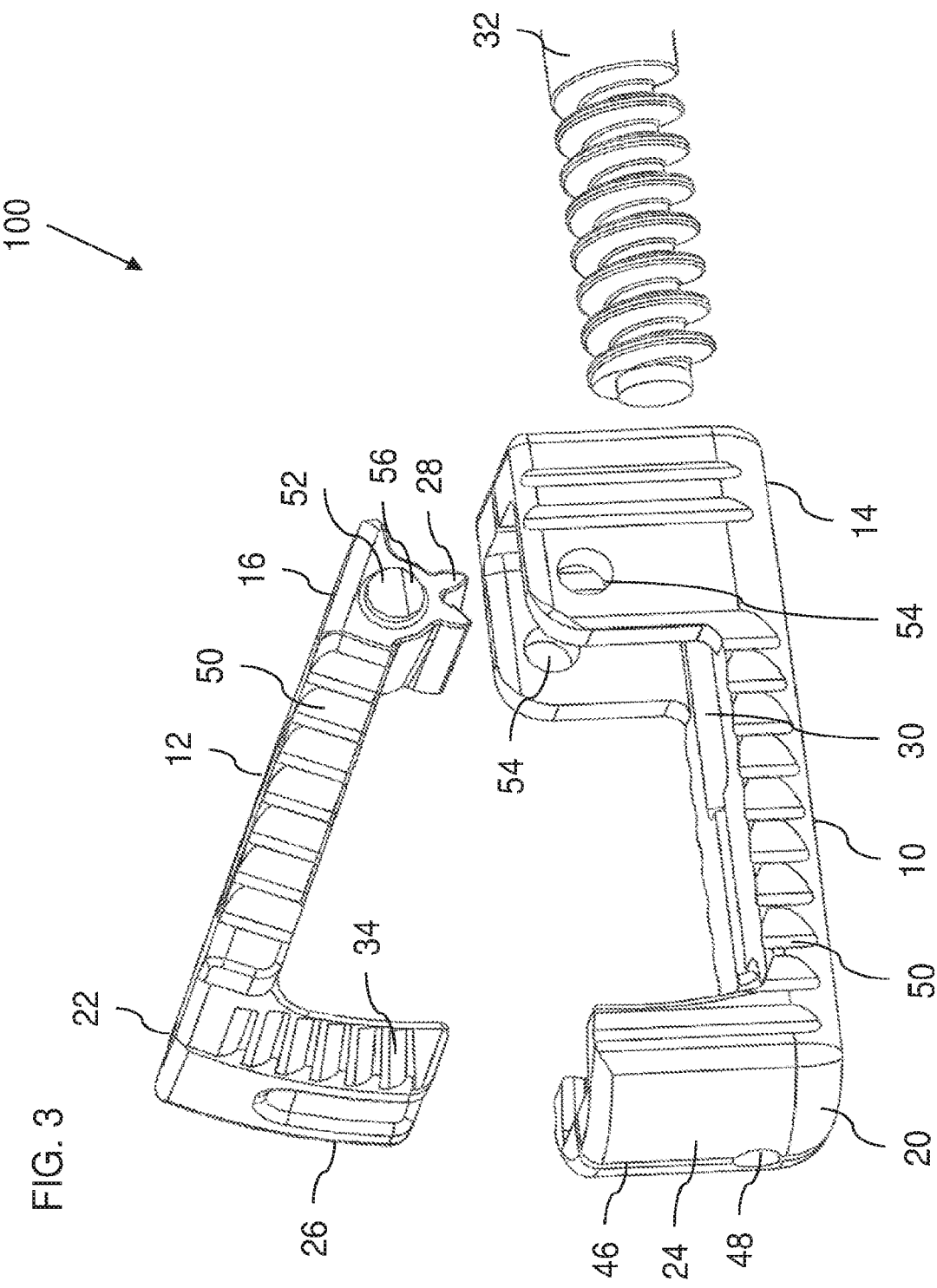
FIG. 3 is an exploded isometric view of the implant of FIG. 1A additionally showing a tip of a worm-gear tool for actuating expansion of the implant.

Expandable implant 100 as illustrated here is particularly adapted for use as an intervertebral cage which expands laterally, i.e., within the intervertebral disc space, as part of an intervertebral fusion procedure. In particular, as best seen in FIGS. 3 and 5B, the leading end of second end portion 20 is here rounded to provide a "bullet nose" effect known to be advantageous for facilitating insertion and minimizing trauma to surrounding tissue during introduction of the device into the body. Expandable implant 100 also features lateral ridges 50 or other projecting features on the edges of base 10 and displaceable element 12 configured to enhance gripping of the adjacent vertebral endplates when the device is deployed.

Turning now to FIGS. 7A and 7B, there is shown a variant implementation of implant 100 labelled 150. Implant 150 is essentially similar in structure and function to implant 100, but differs in that the closed configuration of FIG. 7A is formed with a negative angle between the outer surfaces of base 10 and displaceable element 12, i.e., so that it converges towards end portions 20 and 22, which here form the distal end of the implant. The resulting wedge shape may facilitate introduction of the implant into the body, gradually forcing apart the adjacent tissue. After reaching the target location, the implant is expanded to the desired extent, in the same manner discussed above in relation to implant 100. Although such a variant is only illustrated here in relation to implant 100, it should be noted that each of the implants discussed herein may be implemented with an initial closed state which has parallel, negatively angled, or positively angled outer surfaces.

Turning now to expandable implant 200, illustrated in FIGS. 8A-9B, this is generally similar in structure and function to implant 100, with analogous features labeled similarly. Implant 200 differs from implant 100 primarily in that it is implemented using a worm gear 202 which remains within the body as part of the implant itself. Worm gear 202 is rotatably deployed in a recess 204 within first end portion 14 so as to engage teeth 28. Rotation of worm gear 202 displaces teeth 28 so as to rotate the partial gear about axis 18, thereby effecting displacement of the displaceable element from the initial closed state of FIG. 9A to the any desired position in the range up to the fully open state of FIG. 9B. A driver-receiving socket 206, in this case a hex-socket, is formed in at least a proximal end of worm gear 202 so as to allow driving engagement of a suitable driver tool (not shown) with the worm gear.

The pitch angle of worm gear 202 is preferably chosen so as to provide effective frictional locking of the expandable implant at all points within its range of motion, such that no separate ratchet arrangement or other retention mechanism is typically required. The presence of the worm gear as a part of the implant raises the typical count of main structural components of the implant to three, but the structure remains strikingly simple, reliable and compact.

In order to facilitate delivery of filling material into an internal volume of the implant, worm gear 202 is most preferably here implemented as a hollow worm gear formed with an axial through-bore 208. When deployed with a delivery system similar to that of FIG. 5A, a driver tool (replacing worm gear tool 42 of that figure) is used to rotate worm gear 202 to achieve a desired degree of expansion. Once the desired expansion has been achieved, the driver tool is removed, leaving the delivery system lumen available and aligned with through-bore 208 for introduction of filling material via the axial through-bore into the expandable implant.

In all other respects, the structure and function of expandable implant 200 is similar to that of expandable implant 100, and will be understood by analogy to the above description.

Turning now to expandable implant 300, illustrated in FIGS. 10A-12B, this is generally similar in structure and function to implant 200, with analogous features labeled similarly. Implant 300 differs from implant 200 primarily in that it is implemented with a worm gear deployment mechanism at its distal end rather than its proximal end.

Specifically, expandable implant 300 includes a worm gear 302 rotatably deployed in a recess 304 within first end portion 14 so as to engage teeth 28. Rotation of worm gear 302 displaces teeth 28 so as to rotate the partial gear about axis 18, thereby effecting displacement of the displaceable element from the initial closed state of FIG. 11A to the any desired position in the range up to the fully open state of FIG. 1B. In this case, a driver-receiving socket 306, implemented here as a hex-socket, is formed in the inward-facing end of worm gear 302, and is complemented by an aperture 308 formed in the second end portion 20 of the base and aligned with driver-receiving socket 306 so as to allow driving engagement of a suitable driver tool (not shown) with worm gear 302. For this purpose, jaw 26 is here implemented as a forked element with a central gap aligned with aperture 308, as in implant 100 above.

Figure 6C:
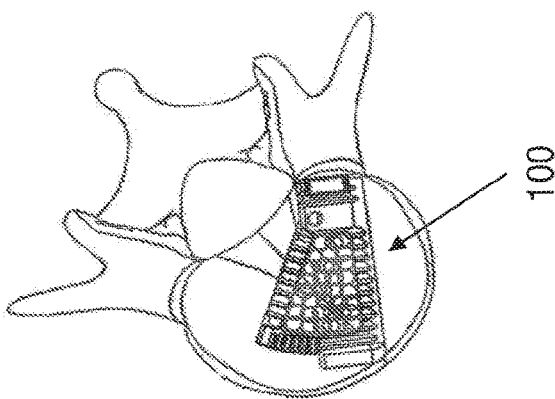
Figure 8A:
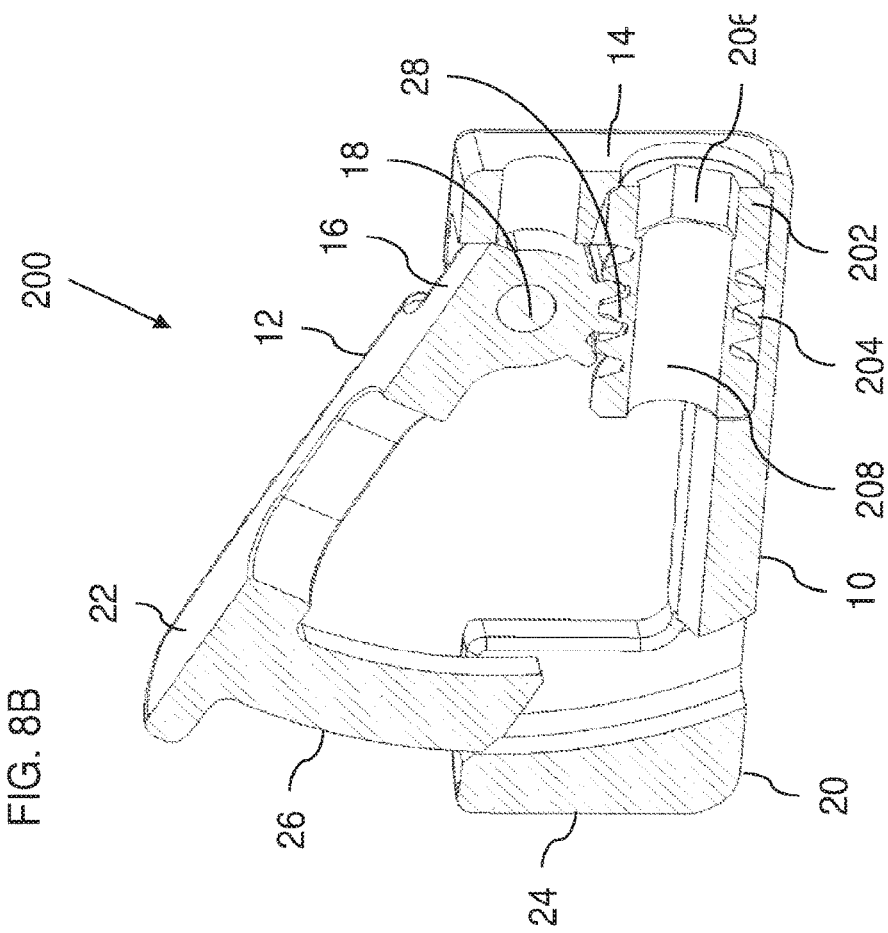
FIG. 8A is an isometric view of an expandable implant, constructed and operative according to a further embodiment of the present invention, shown in an expanded state.
Figure 8B:
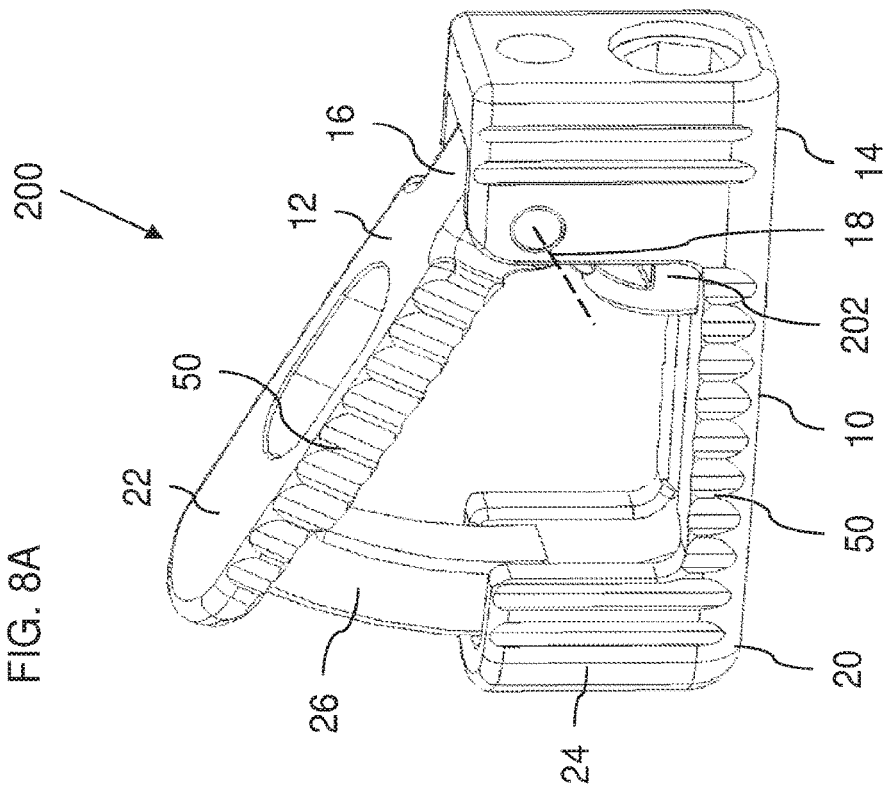
FIG. 8B is a cut-away isometric view similar to FIG. 8A cut along a central longitudinal plane.
Figure 9A:
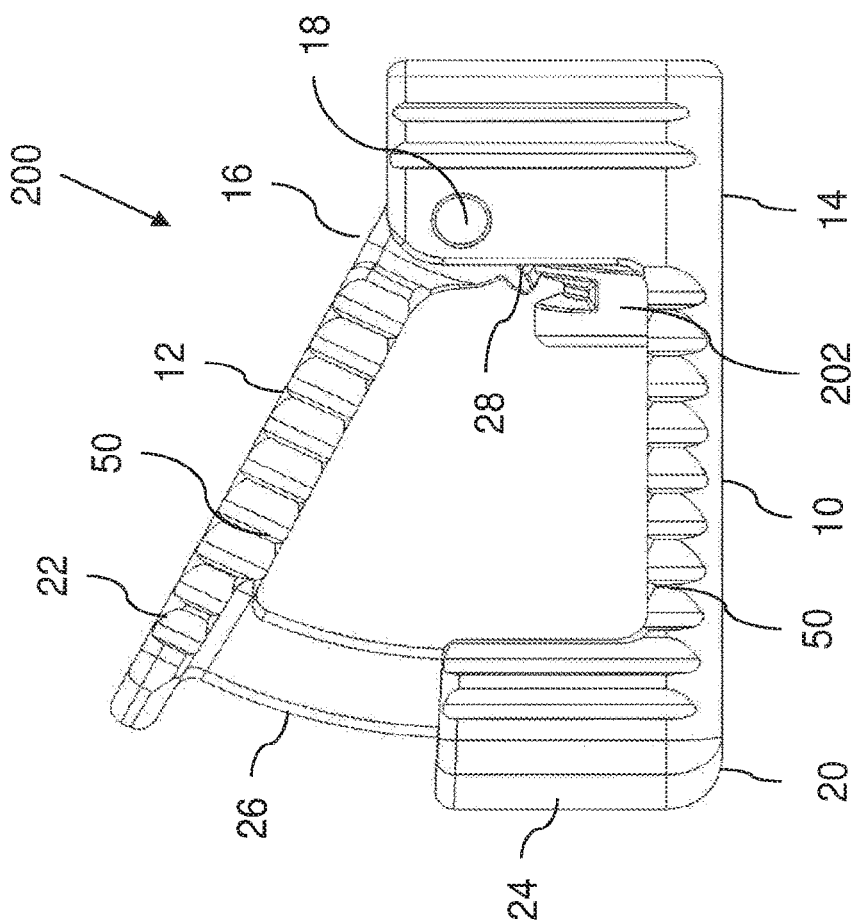
FIGS. 9A and 9B are side views of the implant of FIG. 8A shown in an initial closed state and an expanded state, respectively.
Figure 9B:
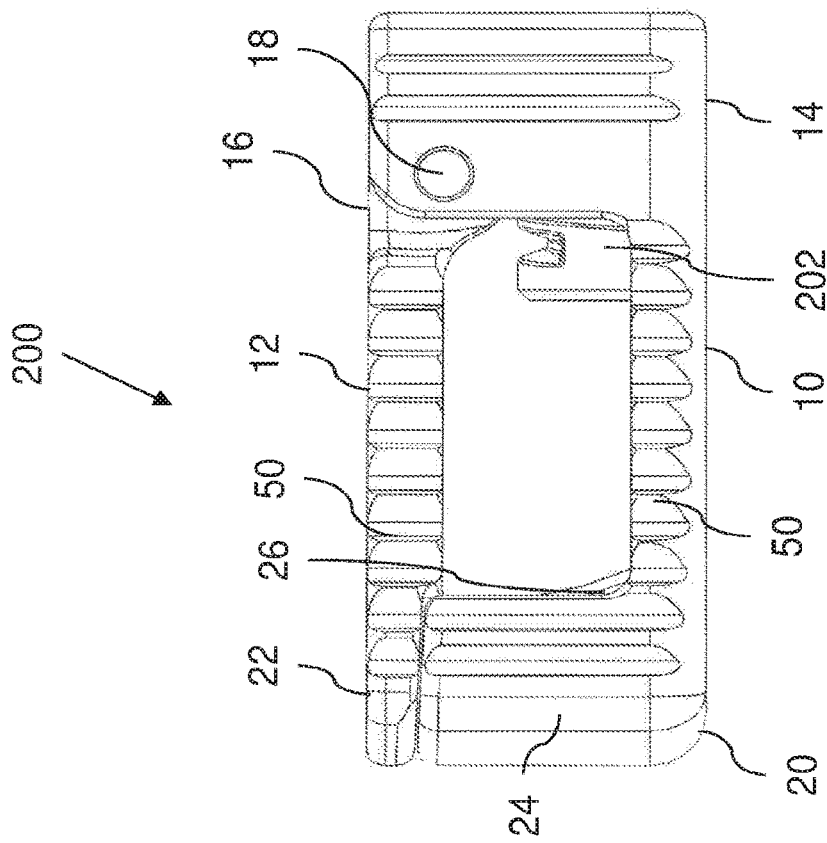
Figure 10A:
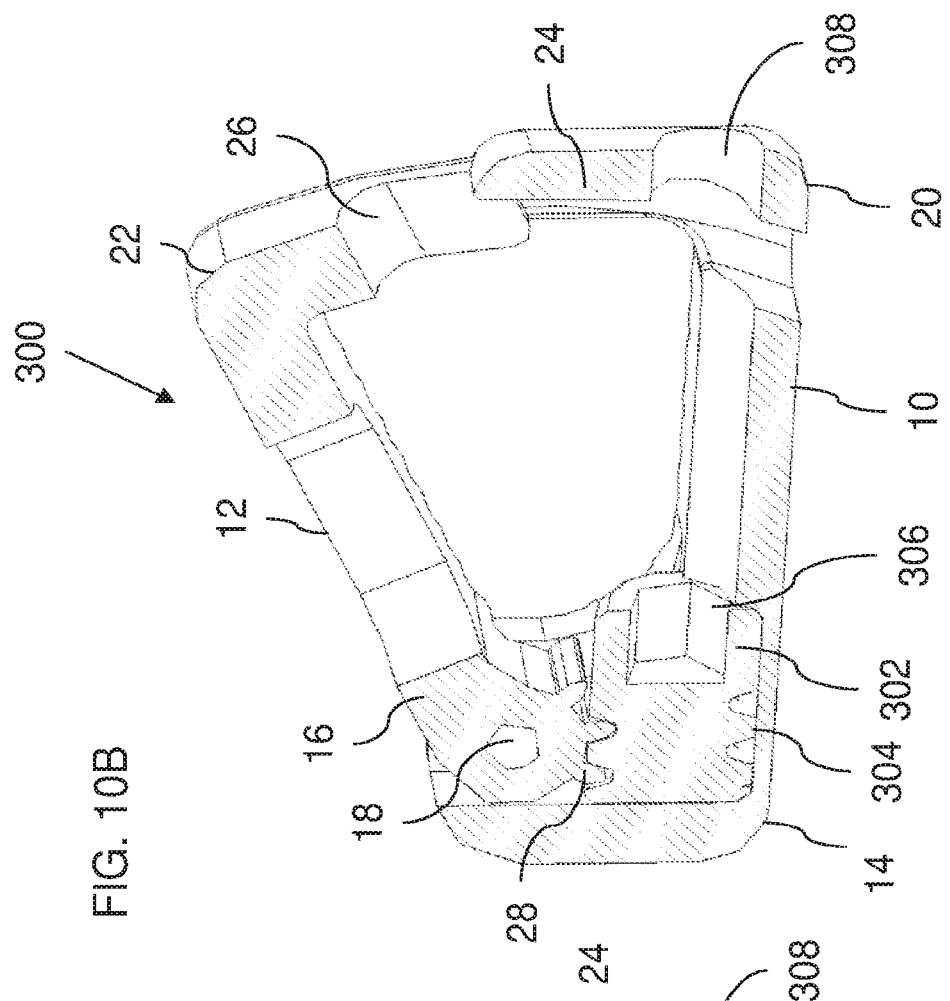
FIG. 10A is an isometric view of an expandable implant, constructed and operative according to a further embodiment of the present invention, shown in an expanded state.
Figure 10B:
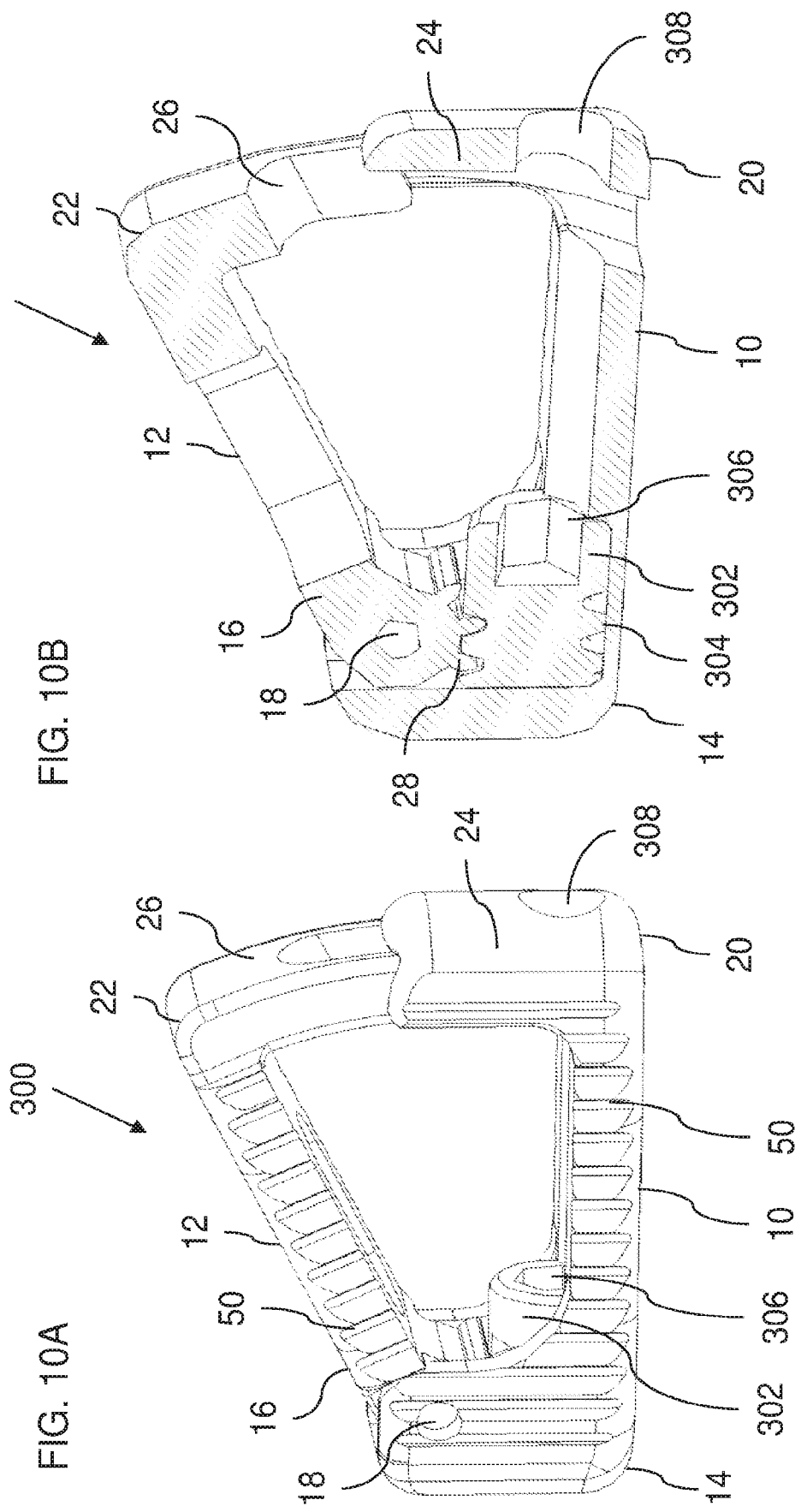
FIG. 10B is a cut-away isometric view similar to FIG. 10A cut along a central longitudinal plane.
Figure 12B:
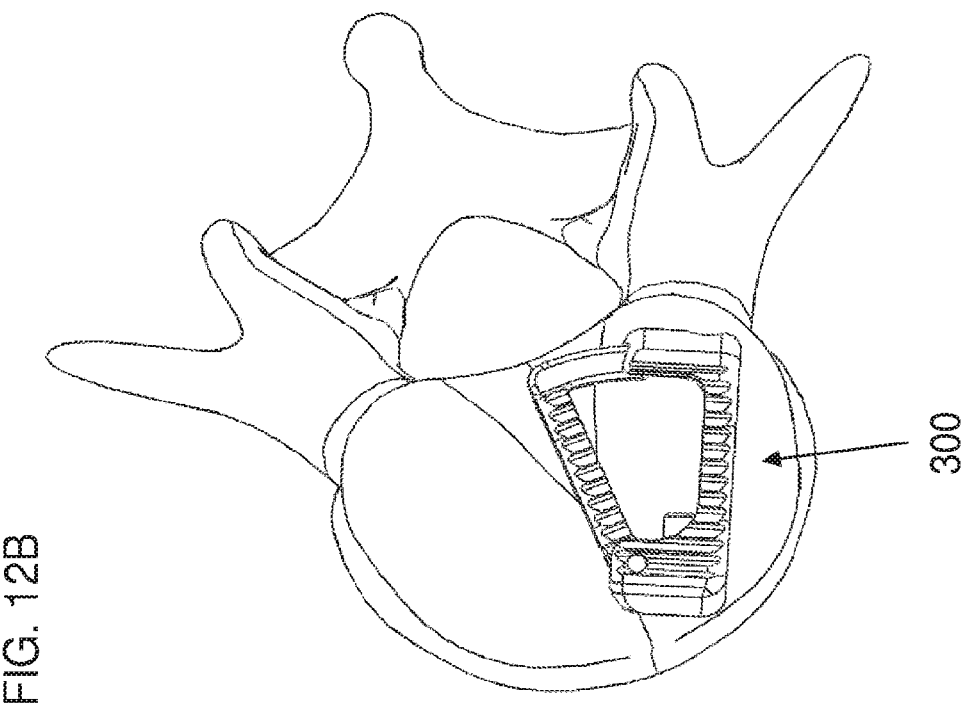
FIGS. 12A and 12B are schematic plan views showing the positioning of the implant of FIG. 10A relative to a vertebra in an initial compact state and in an expanded deployed state, respectively.
Figure 12A:
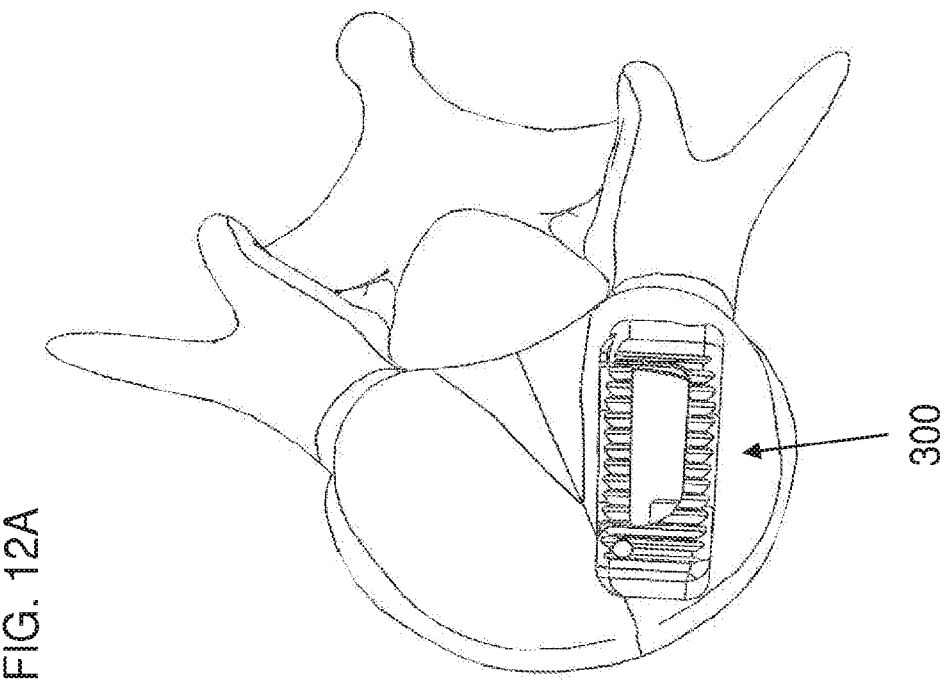
Figure 14A:
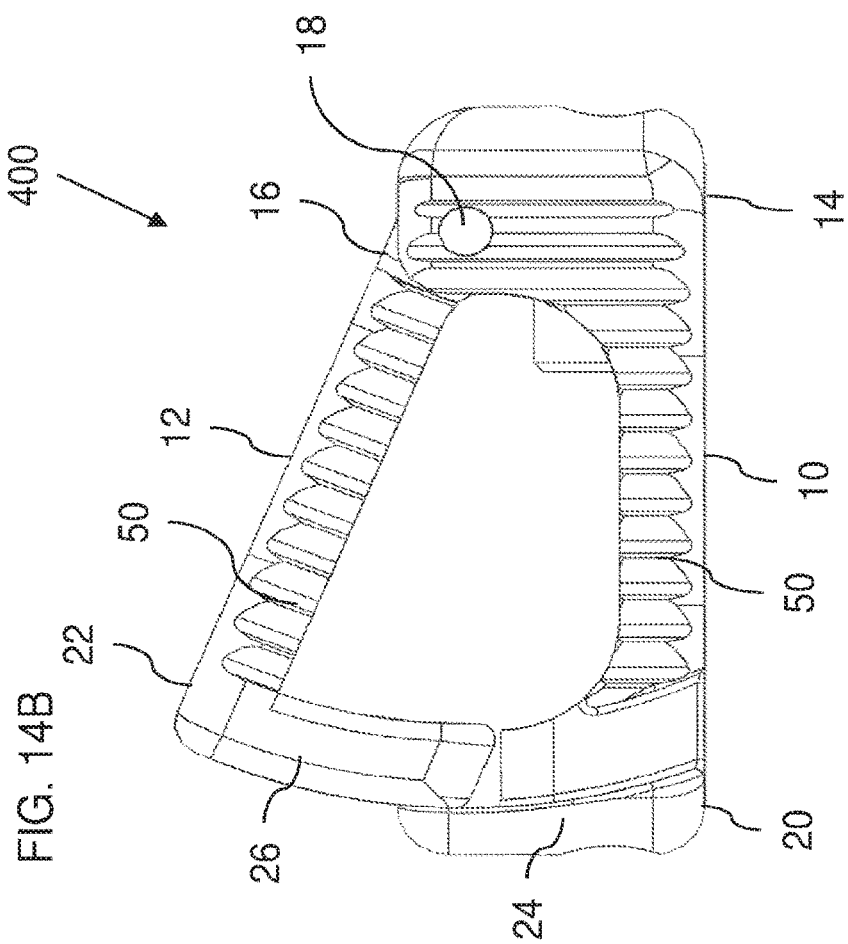
FIGS. 14A and 14B are side views of the implant of FIG. 13A shown in an initial closed state and an expanded state, respectively.
Figure 14B:
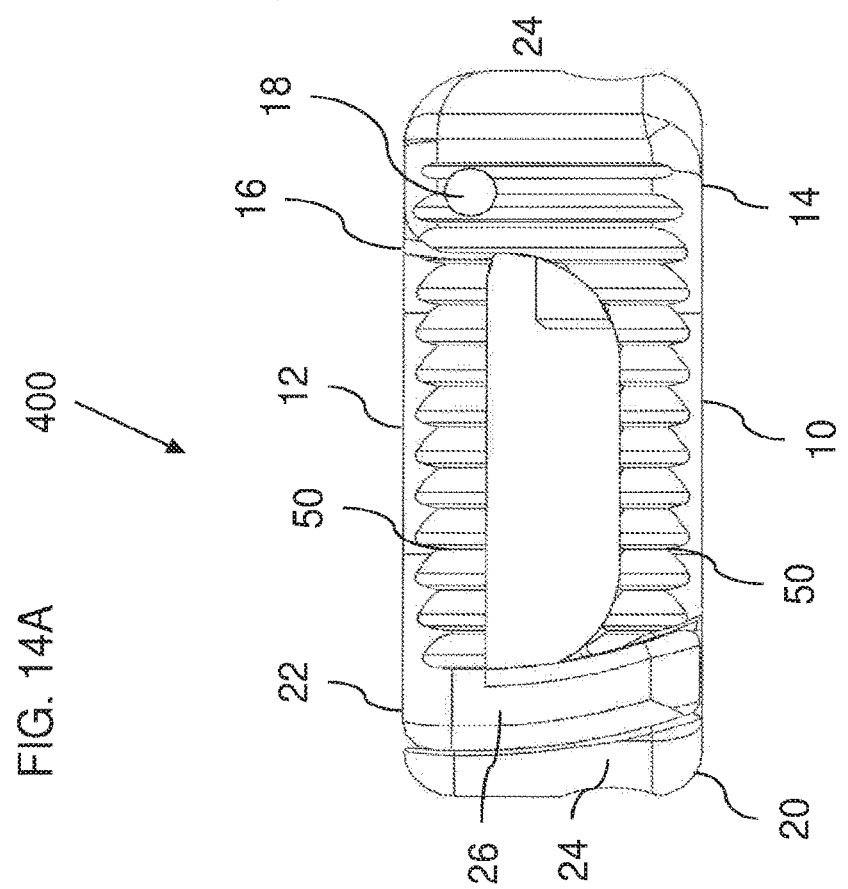

Positioning of the deployment mechanism at the distal end of implant 300 generates a deployment geometry with expansion occurring primarily at the proximal end of the implant when deployed, in contrast to the primarily distal expansion of FIGS. 6B and 6C. A typical position of deployment of implant 300 via a TLIF approach, prior to and after expansion, is shown schematically in FIGS. 12A and 12B, respectively.

In this embodiment, it is first end portion 14 of base 10 that forms the leading (distal) end of the implant during insertion. First end portion 14 is therefore preferably formed with a rounded or "bullet-nose" profile, as best seen in FIG. 11C, in order to facilitate the insertion.

In all other respects, the structure and function of expandable implant 300 is similar to that of expandable implant 200, and will be understood by analogy to the above description.

Turning now to expandable implant 400, illustrated in FIGS. 13A-15B, this implant is conceptually a combination of features from implants 200 and 300, with analogous features labeled similarly. Implant 400 differs from implants 200 and 300 primarily in that it provides accessibility for operating worm gear 202 from either end of the implant, thereby allowing the user to choose whether to deploy the implant with the worm gear mechanism at the proximal or distal end of the implant.

Thus, expandable implant 400 shares with implant 200 a worm gear 202 deployed in a recess 204 with a through-bore 208 which typically is implemented with a hex-socket cross-section so as to serve also as a bidirectional driver-receiving socket. In addition, second end portion 20 of the base is preferably formed with an aperture 308 aligned with worm gear 202 so as to allow insertion of a tool through the aperture to engage the worm gear for rotating the worm gear.

Figure 15A:
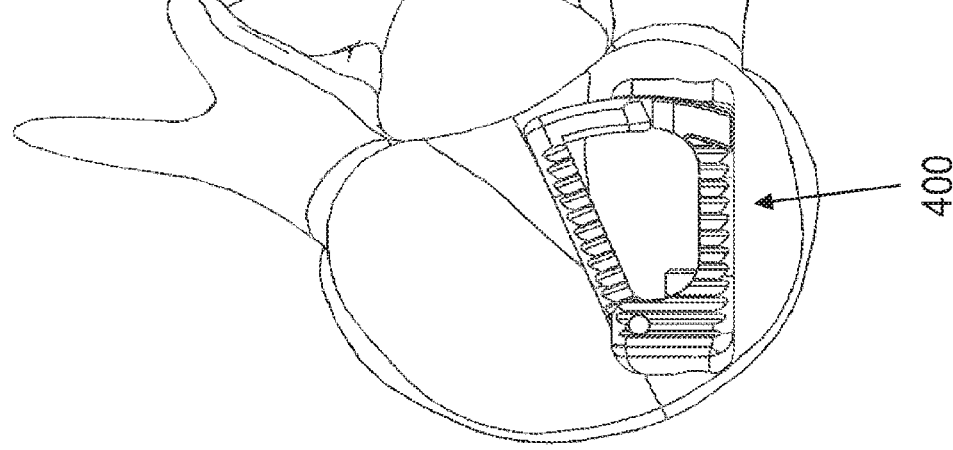
FIGS. 15A and 15B are schematic plan views showing the positioning of the implant of FIG. 13A relative to a vertebra in an expanded deployed state, the implant being shown in a first orientation and a second orientation, respectively.
Figure 15B:
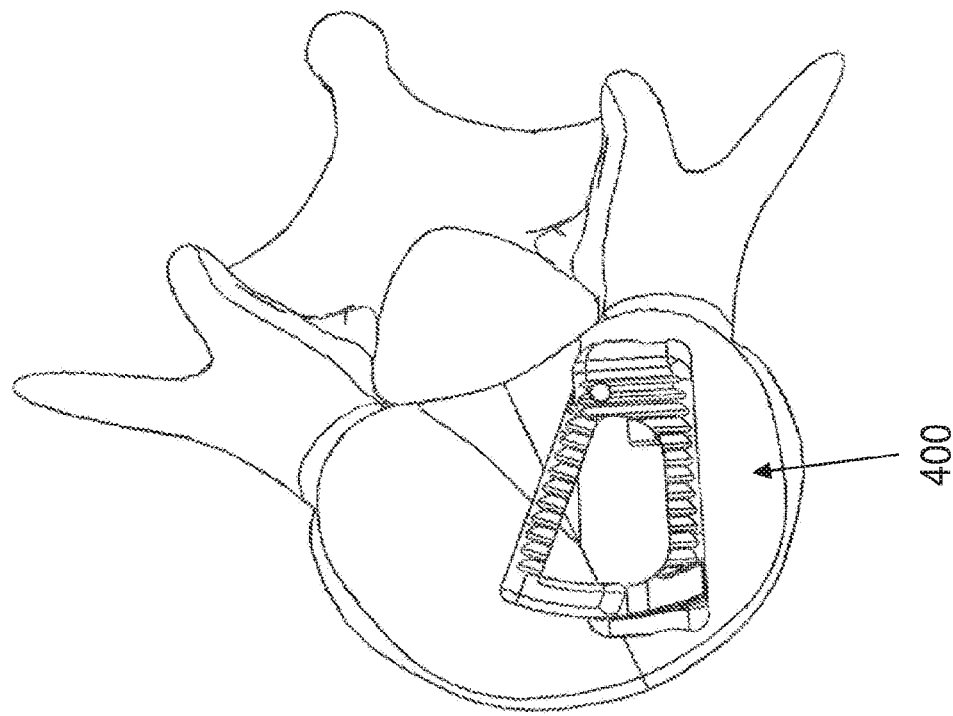

As a result of this structure, expandable implant 400 can be used reversibly, according to the requirements of a particular procedure and the preferences of a particular surgeon. FIG. 15A illustrates schematically a deployed position of expandable implant 400 relative to a vertebral endplate via a TLIF approach when the worm gear mechanism is deployed proximally so as to expand primarily at its distal end. FIG. 15B illustrates schematically a deployed position of expandable implant 400 relative to a vertebral endplate via a TLIF approach when the worm gear mechanism is deployed distally so as to expand primarily at its proximal end.

Expandable implant 400 also illustrates a further variant implementation of overlapping jaws 24 and 26. In contrast to the above embodiments in which jaw 26 is typically circumscribed on three sides by jaw 24, jaw 26 is here implemented a structure which extends the full width of the implant, with a forked structure which straddles a connecting region 402 of base 10, as best seen in FIG. 13A. In the non-limiting example illustrated here, jaw 24 is implemented as an end plate with an arcuate inside surface in facing relation to the arcuate outer surface of jaw 26.

In all other respects, the structure and function of expandable implant 400 is similar to that of expandable implants 200 and 300, and will be understood by analogy to the preceding description.

Turning now to FIGS. 16A-17B, these illustrate a variant implementation of expandable implant 200, designated expandable implant 250. Implant 250 is essentially similar in structure and function to implant 200, with analogous elements labeled similarly. Implant 250 differs from implant 200 primarily in the structure of jaws 24 and 26, which are here arranged as arcuate nested elements with jaw 26 closer to axis 18 and jaw 24 further from the axis. This arrangement allows both jaws to extend across the entire width of the implant. In certain cases, this configuration may provide advantages when used as a laterally expandable intervertebral cage if it is desired to provide enhanced support of around the entire periphery of the cage when deployed.

Parenthetically, although illustrated herein with a generally uniform width, the width dimension of implants according to the present invention may be varied according to the needs of each particular application. For example, in the case of a laterally expandable cage, it may be desirable to vary the width of the implant along its length in order to better fit the implant to the physiological shape of the vertebral endplates.

Figure 18A:
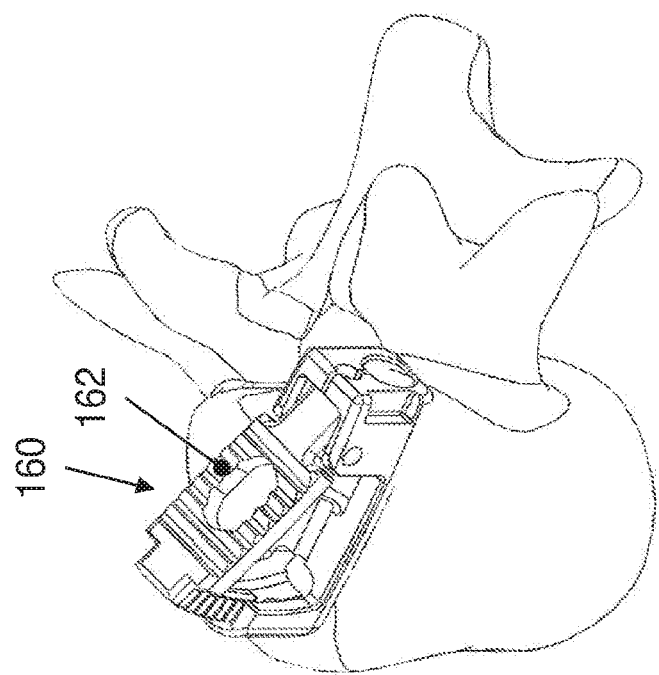
FIGS. 18A and 18B are schematic isometric and plan views, respectively, showing positioning of an expandable implant relative to a vertebra in an expanded deployed state according to a variant embodiment for adjusting lordotic angle between vertebral bodies when inserted via a TLIF approach.
Figure 18B:
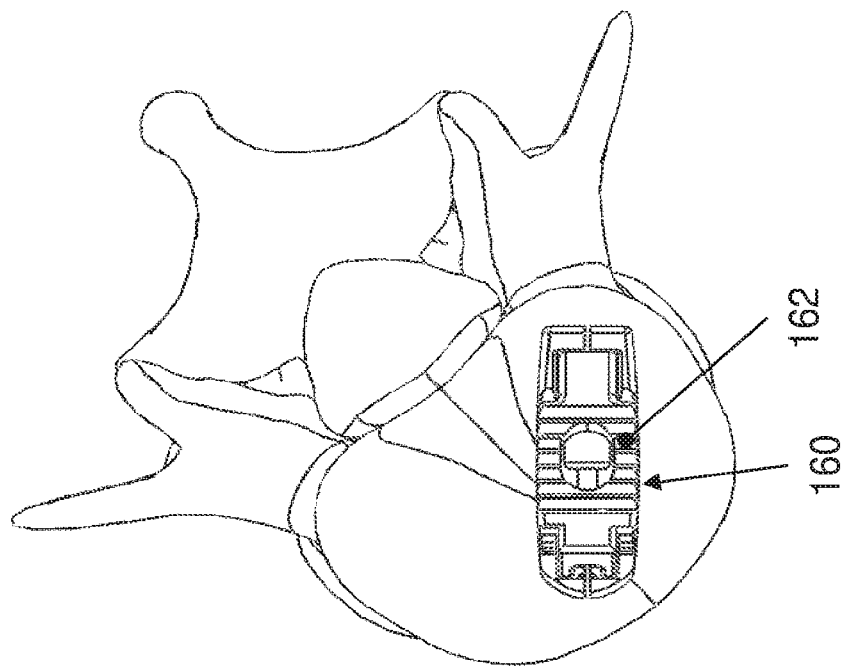
Figure 19B:
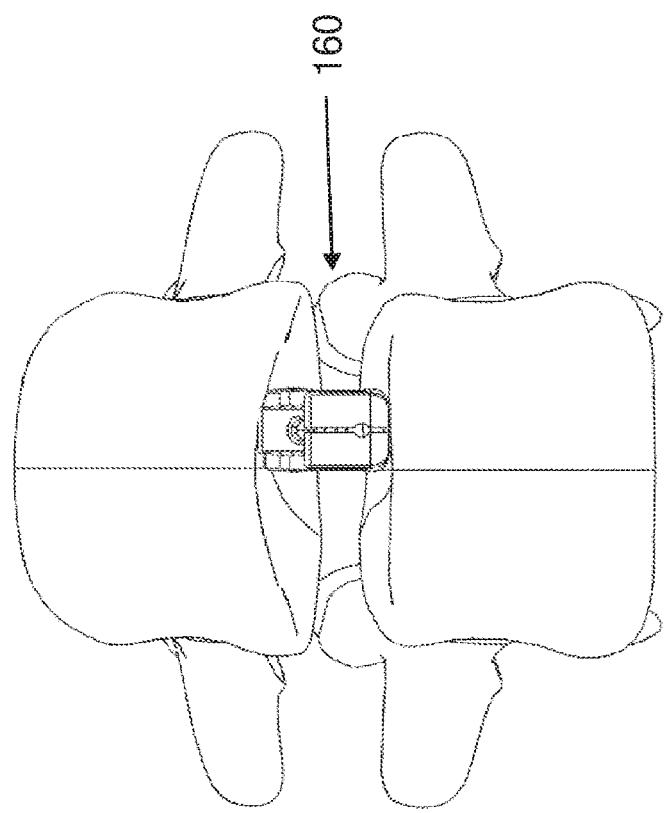
FIGS. 19A and 19B are schematic lateral and anterior views, respectively, showing positioning of the expandable implant of FIGS. 18A and 18B relative to a vertebra in an expanded deployed state when inserted via a PLIF approach.
Figure 19A:
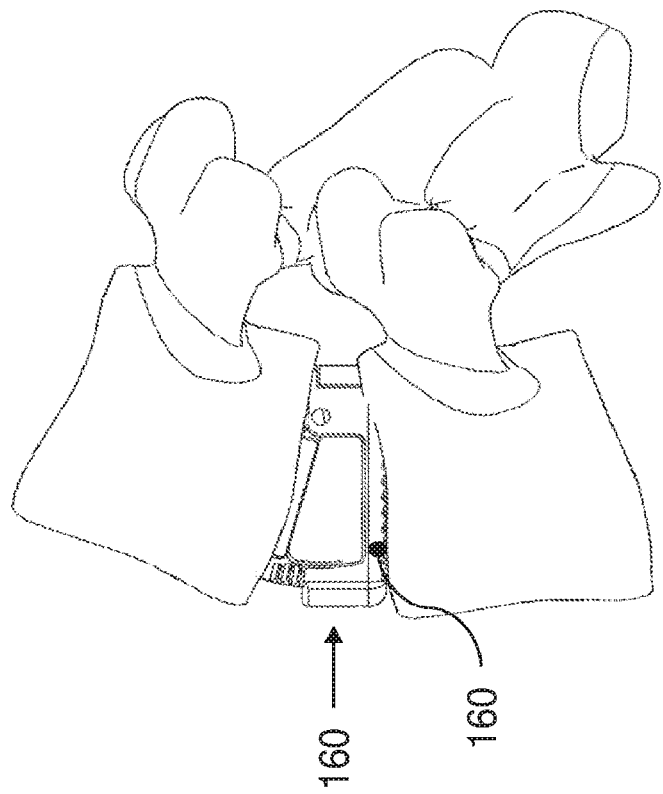
Figure 21A:
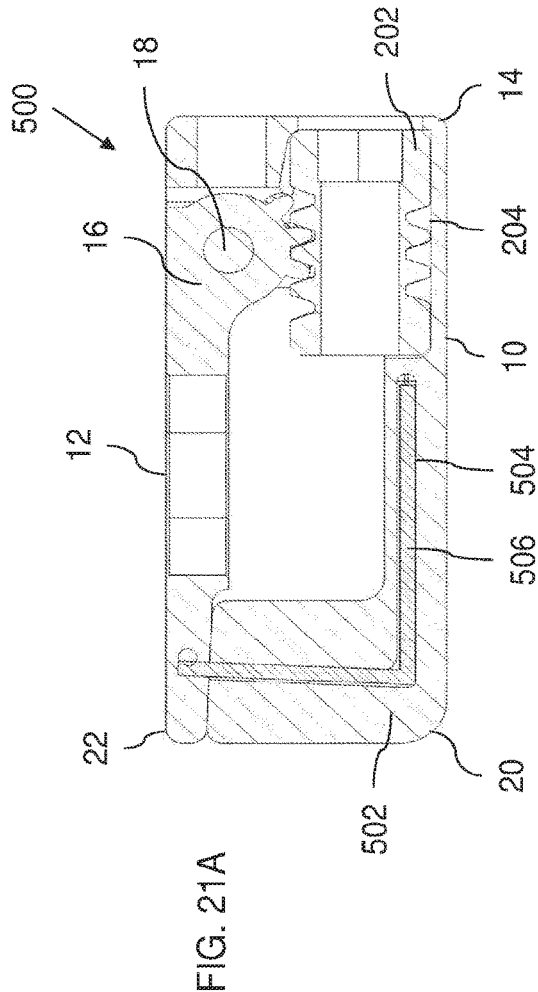
FIGS. 21A and 21B are cross-sectional view taken along a central longitudinal plane of FIG. 20A in an initial closed state and an expanded state, respectively.
Figure 21B:
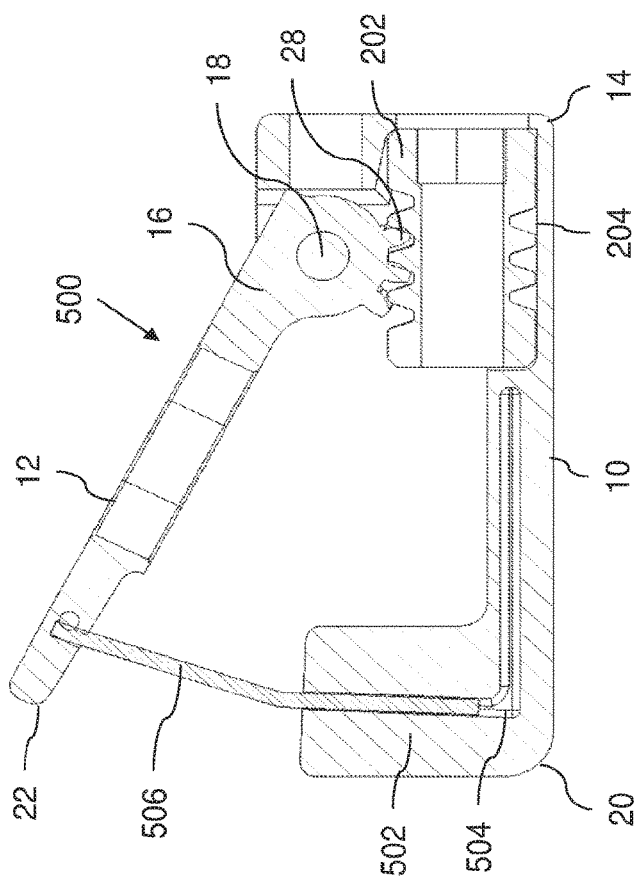

Turning now to FIGS. 18A-19B, although illustrated thus far in the exemplary context of an implant expanding laterally, within an axial plane, it should be noted that the implants of the present invention are not limited to this application, and can equally be used for a range of additional orthopedic applications, whether in spinal surgery or elsewhere in the body. By way of one further subset of non-limiting examples, FIGS. 18A-19B illustrate a modified version of implant 100, here designated 160, configured for use as an angle-correcting implant for adjusting a lordotic angle and/or a scoliosis angle between adjacent vertebral endplates. In this case, instead of providing ridges 50 along the lateral edges of the components, base 10 and displaceable element 12 are here provided with ridges 162 or other projecting features for bone engagement on the major outward facing surfaces of the base and displaceable element. FIGS. 18A and 18B illustrate deployment of expandable implant for restoration of lordotic angle via a TLIF approach, while FIGS. 19A and 19B illustrate deployment via a PLIF approach.

The angular range of motion for which each of the above examples is designed varies according to the requirements of each application. For lordotic or scoliosis angle correction, in some cases, angular ranges of up to 8 degrees may be sufficient. In many cases, it is desirable to provide larger ranges of adjustment, preferably in excess of 10 degrees, and in many cases of 20 degrees or more. Particularly for laterally expandable cage implementations, a maximum opening angle in the range of 20-30 degrees may be preferred.

Referring finally to FIGS. 20A-21B, there is shown an expandable implant, generally designated 500 which exemplifies an alternative approach to maintaining an enclosed volume within the implant during angular deployment of a displaceable element 12 relative to a base 10. The features of implant 500 are generally similar to those of implant 200 described above, and analogous features are labelled similarly. In this case, instead of overlapping jaws, second end portion 20 of base 10 is formed with a hollow block 502 that houses a channel 504 within which is housed a flexible strip 506. One end of flexible strip 506 is fastened to second end portion 22 of displaceable element 12 so that the strip is drawn out and deployed as displaceable element 12 opens away from base 10. Optionally, a mechanism (not shown) may be deployed to maintain tension in the strip.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

The invention claimed is:

1. An expandable implant comprising:
a base having a rigid body extending from a first end portion to a second end portion;
a displaceable element having a rigid body extending from a first end portion to a second end portion, wherein said first end portions of said base and said displaceable element are hingedly interconnected by a hinged interconnection, and wherein said second end portions of said base and said displaceable element are formed with complementary jaws rigidly projecting therefrom, wherein said complementary jaws provide complementary facing arcuate surfaces, and wherein said complementary facing arcuate surfaces of said complementary jaws being configured to provide continuous overlap over a range of angular positions of said displaceable element relative to said base; and
wherein a first jaw of said complementary jaws comprises at least one projecting portion that is interposed between inward facing surfaces of a second of said complementary jaws, wherein said at least one projecting portion and said inward facing surfaces are substantially perpendicular to an axis of said hinged interconnection connecting said first end portions of said base and said displaceable element, and wherein said first end portion of said displaceable element is formed with a plurality of projecting teeth configured as a partial gear centered on said axis of said hinged interconnection with said base.

2. The expandable implant of claim 1, wherein said complementary jaws provide complementary facing surfaces forming solids of revolution about said axis of said hinged interconnection.

3. The expandable implant of claim 2, further comprising a worm gear rotatably deployed within said first end portion of said base in engagement with said plurality of projecting teeth such that rotation of said worm gear effects displacement of said displaceable element, wherein said worm gear is a hollow worm gear formed with an axial through-bore for introduction of filling material via said axial through-bore into the expandable implant.

4. The expandable implant of claim 2, further comprising a worm gear rotatably deployed within said first end portion of said base in engagement with said plurality of projecting teeth such that rotation of said worm gear effects displacement of said displaceable element, and wherein said second end portion of said base is formed with an aperture aligned with said worm gear so as to allow insertion of a tool through said aperture to engage said worm gear for rotating said worm gear.

5. The expandable implant of claim 1, wherein said inward facing surfaces are integrated with an end wall such that said inward facing surfaces and said end wall encompass said at least one projecting portion on three sides.

6. The expandable implant of claim 1, wherein said complementary jaws are configured to provide said continuous overlap over a range of angular positions of said displaceable element relative to said base spanning at least 10 degrees.

7. The expandable implant of claim 1, wherein said complementary jaws are configured to provide said continuous overlap over a range of angular positions of said displaceable element relative to said base spanning at least 20 degrees.

8. The expandable implant of claim 1, wherein said plurality of projecting teeth are configured for engaging a worm gear.

9. The expandable implant of claim 8, wherein said first end portion of said base is formed with a socket configured for removably receiving a worm gear tool for engaging said teeth and displacing said displaceable element.

10. The expandable implant of claim 8, wherein said second end portion of said base is formed with an aperture aligned with said worm gear so as to allow insertion of a tool through said aperture to engage said worm gear for rotating said worm gear.

11. The expandable implant of claim 1, wherein said displaceable element is displaceable relative to said base from an initial position defining a compact configuration of the expandable implant towards a deployed position defining an expanded configuration of the expandable implant, and wherein said complementary jaws are formed with complementary parts of a retention configuration configured for inhibiting return of said displaceable element towards said initial position.

12. The expandable implant of claim 11, wherein said retention configuration comprises at least one sequence of ratchet teeth deployed to inhibit return of said displaceable element from a range of positions of said displaceable element towards said initial position.

13. The expandable implant of claim 11, wherein said retention configuration comprises two resilient retention elements separated by a slot, and wherein said retention configuration is configured such that, on insertion of a prising tool into said slot to increase a spacing of said slot, said retention configuration is released to allow displacement of said displaceable element towards said initial position.

14. An expandable implant comprising:
a base having a rigid body extending from a first end portion to a second end portion; and
a displaceable element having a rigid body extending from a first end portion to a second end portion, wherein said first end portions of said base and said displaceable element are hingedly interconnected by a hinged interconnection, and wherein said first end portion of said displaceable element is formed with a plurality of projecting teeth form a partial gear centered on an axis of said hinged interconnection with said base, said projecting teeth being configured for engaging a worm gear, and wherein said first end portion of said base is formed with a socket configured for removably receiving a worm gear tool for engaging said teeth and displacing said displaceable element; and
wherein said second end portions of said base and said displaceable element are formed with complementary jaws rigidly projecting therefrom, wherein a first jaw of said complementary jaws comprises at least one projecting portion that is interposed between inward facing surfaces of a second of said complementary jaws, wherein said at least one projecting portion and said inward facing surfaces are substantially perpendicular to an axis of said hinged interconnection connecting said first end portions of said base and said displaceable element.

15. The expandable implant of claim 14, said complementary jaws being configured to provide continuous overlap over a range of angular positions of said displaceable element relative to said base.

\* \* \* \* \*